(12) United States Patent
Cates

(10) Patent No.: US 11,317,176 B2
(45) Date of Patent: Apr. 26, 2022

(54) SYSTEMS AND METHODS FOR SENSOR MONITORING AND SENSOR-RELATED CALCULATIONS

(71) Applicant: Lizard Monitoring LLC, Portland, OR (US)

(72) Inventor: Terry Cates, Santa Rosa, CA (US)

(73) Assignee: LIZARD MONITORING LLC, Portland, OR (US)

( * ) Notice: Subject to any disclaimer, the term of this patent is extended or adjusted under 35 U.S.C. 154(b) by 109 days.

(21) Appl. No.: 16/811,916

(22) Filed: Mar. 6, 2020

(65) Prior Publication Data

US 2020/0288218 A1 Sep. 10, 2020

Related U.S. Application Data

(60) Provisional application No. 62/815,218, filed on Mar. 7, 2019.

(51) Int. Cl.
*G01K 1/022* (2021.01)
*G01K 1/024* (2021.01)
*G01N 33/00* (2006.01)
*H04Q 9/00* (2006.01)
*G01K 3/00* (2006.01)

(52) U.S. Cl.
CPC ............. *H04Q 9/00* (2013.01); *G01K 1/022* (2013.01); *G01K 1/024* (2013.01); *G01K 3/005* (2013.01); *G01N 33/0036* (2013.01); *H04Q 2209/10* (2013.01); *H04Q 2209/82* (2013.01); *H04Q 2209/84* (2013.01)

(58) Field of Classification Search
None
See application file for complete search history.

(56) References Cited

U.S. PATENT DOCUMENTS 7,027,958 B2 * 4/2006 Singh ................. G05B 23/0272
340/585
2013/0227971 A1 * 9/2013 Tamborra ............. F25D 29/008
62/62

(Continued)

FOREIGN PATENT DOCUMENTS

WO WO-2004063124 A1 * 7/2004 ............... B28B 1/08

*Primary Examiner* — Curtis A Kuntz
*Assistant Examiner* — Jerold B Murphy
(74) *Attorney, Agent, or Firm* — Stoel Rives LLP

(57) ABSTRACT

Systems and methods for temperature monitoring and environmentally related calculations are disclosed herein. A system according to embodiments herein may include a memory, a network interface, and one or more processors. The system may receive one or more environmental readings from a sensor taking readings at an environmentally controlled area. The system may further determine a timestamp corresponding to each of the one or more readings and calculate, using the one or more readings and their corresponding timestamps, an exposure of a good stored within the temperature controlled area. The system may further determine that the calculated exposure of the good has surpassed a pre-determined exposure threshold for the good and send an electronic message configured to indicate such determination to a user. The system may use a neural network to predict future readings based on current readings and use the predicted future readings in methods described herein.

20 Claims, 14 Drawing Sheets

(56) References Cited

U.S. PATENT DOCUMENTS

| | | | |
|---|---|---|---|
| 2015/0048938 A1* | 2/2015 | Tew | G08B 21/182 340/517 |
| 2018/0003572 A1* | 1/2018 | Garsd | G01K 3/14 |
| 2020/0097776 A1* | 3/2020 | Kim | G06T 7/97 |

* cited by examiner

History — 56 Entries

[1] [2] [3] [4] [5] [6] [Next]

⚠ Open  2.7 degree-hours of exposure
Cause:
This sensor became too warm starting on Mar 15th 2018 at 2:52 am
Notifications:
📞 on Mar 15th at 3:52 am
[Show on Graph] [Provide Resolution]

● Open  2.7 degree-hours of exposure
Cause: Cleaning Case
This sensor became too warm starting on Mar 15th 2018 at 2:52 am
Notifications:
📞 on Mar 15th at 3:52 am
Resolution:
On Mar 3rd 2018 at 3:40 am Shawn Tardy wrote: *no product in case*
[Show on Graph] [Provide Resolution]

● Open  2.7 degree-hours of exposure
Cause: Door left open
This sensor became too warm starting on Mar 2nd 2018 at 2:47 am
Notifications:
📞 on Mar 2nd 2018 at 3:47 am
📞 on Mar 2nd 2018 at 4:17 am
Resolution:
On Mar 2nd 2018 at 8:53 pm James P wrote: *Pulling product out of case*
[Show on Graph] [Provide Resolution]

US 11,317,176 B2

SYSTEMS AND METHODS FOR SENSOR MONITORING AND SENSOR-RELATED CALCULATIONS

CROSS-REFERENCE TO RELATED APPLICATIONS

This application claims priority to U.S. Provisional Application No. 62/815,218 entitled "SYSTEMS AND METHODS FOR TEMPERATURE MONITORING AND TEMPERATURE-RELATED CALCULATIONS," filed on Mar. 7, 2019, which is hereby incorporated by reference in its entirety.

BACKGROUND

Keeping environmentally sensitive goods within the appropriate range for a relevant environmental characteristic (e.g., temperature, humidity) is important to keep the good from incurring environmental related damage (e.g., bacterial growth or other spoliation). However, current systems and methods for collecting data about and/or monitoring relevant environmental conditions affecting such environmentally sensitive goods are fragmented and incomplete, and lack useful functionality for those responsible for ensuring the integrity of the good.

TECHNICAL FIELD

The disclosure relates generally to the collection and use of environmental data (e.g., temperature, humidity).

BRIEF SUMMARY

The present disclosure provides embodiments of computer-implemented systems and methods for sensor monitoring and sensor-related calculations.

BRIEF DESCRIPTION OF THE SEVERAL VIEWS OF THE DRAWINGS

FIG. 9 illustrates a display for configuring alert parameters for a sensor, according to embodiments discussed herein.

FIG. 10 illustrates a display for providing audit data in the form of alert resolutions, according to an embodiment.

DETAILED DESCRIPTION

Figure 1:
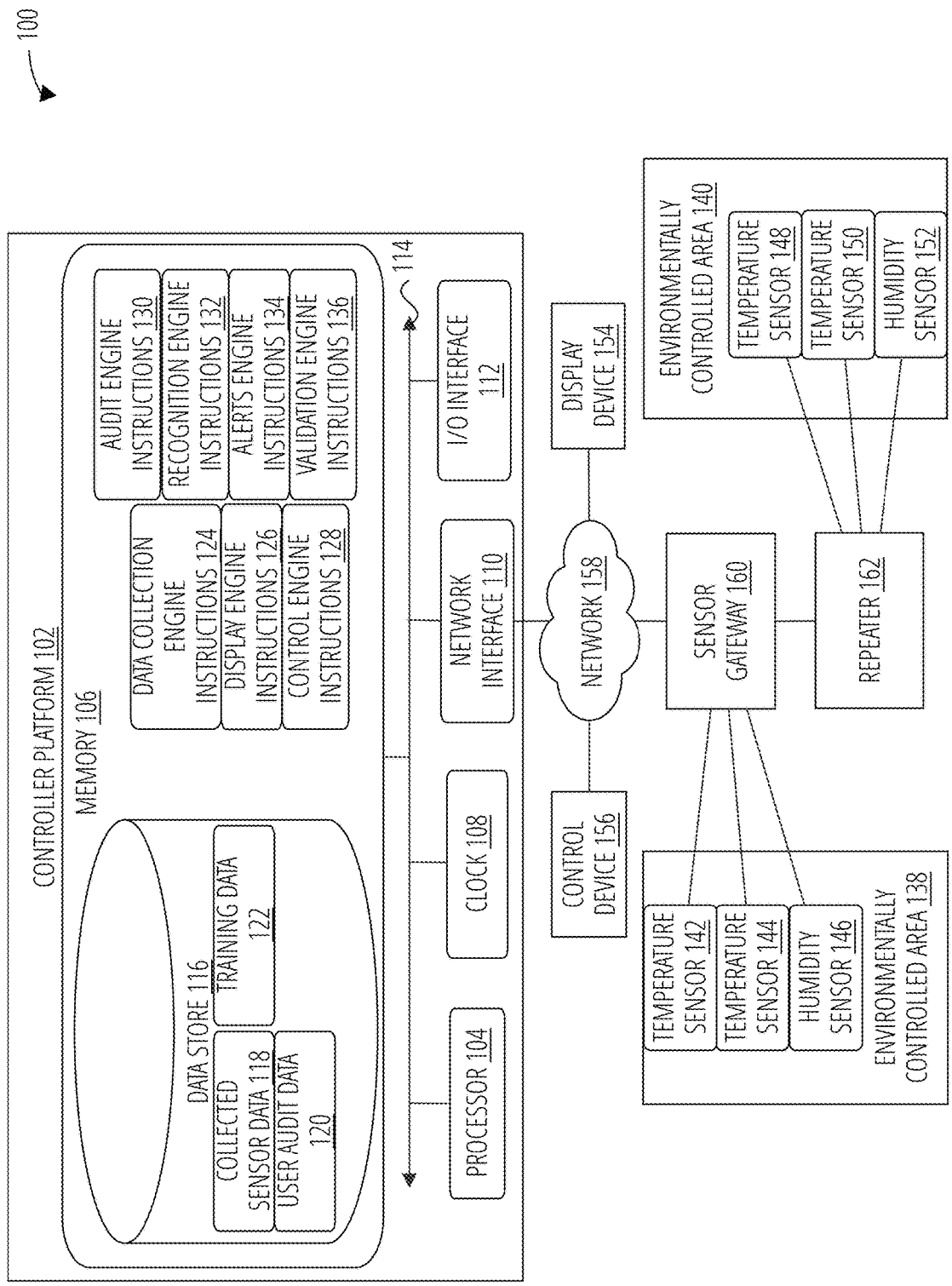
FIG. 1 illustrates a system for sensor monitoring and sensor-related calculations, according to an embodiment.

The collection and analysis of sensor information related to environmentally sensitive goods allows a vendor to know of and properly react to key circumstances in relation to environmentally sensitive goods. For example, many goods (e.g., certain foodstuffs and pharmaceuticals) depend on the proper maintenance of a specified ambient temperature inside a container housing the good to prevent the good from spoiling prior to use. A vendor may wish to ensure that the interiors of containers holding any such environmentally sensitive goods the vendor offers for sale are kept within given temperature limits over time so that the vendor can be assured that goods are unspoiled. Further, a vendor may be required by law or regulation to track the temperature inside the container housing the good for reporting or other reasons. The terms "good" and "product" may be used interchangeably herein.

Manual methods of collection and analysis of environmental information for goods have certain drawbacks. For example, some manual methods inherently require a person to be on-site so that that person can personally perform and record an environmental measurement of a designated location at a designated time. Under these methods, a manual reading may need to be performed up to four to five (or more) times per day. The effectiveness of these manual systems is thus premised on both the presence of one or more persons to be at the site and the capability of these one or more persons to take accurate environmental readings in the proper way at the proper location and at the proper time.

The staffing and training requirements of these manual methods have associated costs. These costs may be prohibitive to taking environmental readings with a frequency that may otherwise be desirable. Further, the manual collection of environmental readings can be inaccurate and/or untimely due to human error or human inconsistency (e.g., when a human operator performs an environmental reading in the wrong way, in an incorrect location, and/or at the incorrect time). Oversight costs may need to be incurred in some circumstances in order to ensure that manual environmental readings are being taken correctly.

In manual environmental data collection systems, there is often no central governance and only limited visibility of the collected environmental data (and its manner of collection). To enable an analysis of the manually collected data at a certain location over time (or to enable any analysis of data taken over time across different environmental reading locations), this manually collected data may need to be further collected and compiled. This collection and compilation process may also have attendant costs. As used herein, the phrase "over time" in relation to a set of data may refer generally to the idea that data points of the data set are to be understood to have corresponding timestamps representing a time at which a data point of the set was collected (or, for calculated data sets, the time at which an underlying collected data point associated with the calculated data point was collected).

In many cases, it may be further desirable to use the collected data to determine other data points related to the taken environmental readings. For example, for methods measuring the ambient temperatures around a given good or goods, it may be desirable to use mathematical modeling methods to determine the effect of the ambient temperature surrounding the good over time on the temperature of the good itself. It may also be desirable to use that calculated temperature data regarding a good itself in further mathematical calculations. The calculation of these related data points may require the use of mathematical methods that are unfamiliar to a possessor of compiled, manually collected environmental readings. It may also be that even if the mathematical methods are familiar to the possessor, the calculation of these data points by the compiler would be time-consuming and prone to error. It may also be that simply uploading the manually collected environmental readings into a computer system that can perform these mathematical method on the manually collected environmental readings may be more time-consuming and/or expensive than is merited.

Automated systems performing the collection and compilation of environmental readings (and/or the calculation of other information based on these readings) can aid a vendor of environmentally sensitive goods to overcome issues associated with manual methods of environmental data collection. Automated systems may also aid the vendor in achieving product environmental monitoring, legal compliance, and other important goals.

Automated systems according to embodiments herein may be capable of taking measurements at a much higher frequency than would be feasible with a manual method. Further, the automatic compilation of data by the system means that a user of the system can quickly and easily view the collected data for quality assurance and reporting purposes.

Other benefits that a system according to embodiments herein may enjoy over manual collection methods is the ability of a user to more simply view and analyze data that has been collected over a long period of time in order to determine whether a notable pattern is occurring. The system may provide a manner for a user to conveniently view a set of temperature data points graphed according to a specified period of time.

The collection, display, and use of environmental data points in the manners disclosed herein may help alleviate the insufficiencies and inconsistencies attendant with using manual environmental data collection methods. An automated system for the taking of an environmental reading from a sensor may remove or ameliorate the costs associated with staffing and training persons to properly perform the environmental data collection. The use of a placed sensor helps ensure that the same location is measured every time in the same manner.

An automated system is especially most useful to a user when it performs and/or allows the accurate interpretation of environmental readings and other environmentally-related information. However, looking for trends and problems in this data presents technological challenges. One of these is that for some systems, given environmental measurements represent a "dirty/noisy" form of data. For example, temperature readings in almost all retail refrigeration cases fluctuate significantly with physical position of the sensor, ambient temperature, the design of the case, and other possible factors (such as, e.g., the existence and condition any defrost controller in the refrigerator). Generating useful, actionable results (e.g., alerts) from data gathered under these types of conditions requires innovation. Accordingly, the automated systems described herein may analyze data to arrive at such actionable results.

FIG. 1 illustrates a system 100 for sensor monitoring and sensor-related calculations, according to an embodiment. A system 100 according to embodiments herein may include a controller platform 102. The controller platform 102 may include a processor 104, a memory 106, a clock 108, a network interface 110, and/or an I/O interface 112. Each of these elements may be connected via a bus 114, which may allow for electrical communication, signaling and other data transport between these elements.

The memory 106 of the controller platform 102 may include a data store 116. The data store 116 may include collected sensor data 118, user audit data 120, and training data 122. The memory 106 may further include data collection engine instructions 124, display engine instructions 126, control engine instructions 128, audit engine instructions 130, recognition engine instructions 132, alerts engine instructions 134, and/or validation engine instructions 136. The memory 106 may be volatile memory (e.g., Random Access Memory (RAM)), non-volatile memory (e.g., flash memory), or any combination of volatile and non-volatile memory.

The controller platform 102 may be implemented using one or more pieces of computer hardware and may further be comprised of one or more pieces of software running on the one or more pieces of computer hardware. The controller platform 102 may be a cloud-based controller platform.

The system 100 may further include an environmentally controlled area 138 and/or an environmentally controlled area 140. Each of the environmentally controlled area 138 and/or the environmentally controlled area 140 may be, for example, a refrigerator interior (whether enclosed or open-air), a humidity controlled enclosure, or the like. The environmentally controlled area 138 may include one or more sensors, including a temperature sensor 142, a temperature sensor 144, and/or a humidity sensor 146. Each of the environmentally controlled area 138 and the environmentally controlled area 140 may be individually controlled for temperature, controlled for humidity, controlled for temperature and humidity, etc.

It may be that each of the temperature sensor 142, the temperature sensor 144, and/or the humidity sensor 146 connect to a sensor gateway 160 via one or more wires. It may be that the temperature sensor 142, the temperature sensor 144, and the humidity sensor 146 connect to the sensor gateway 160 wirelessly. In the wired case, it may be that the sensor gateway 160 provides power to one or more of the sensors for the sensors to operate via the wires. These sensors may communicate with the sensor gateway 160 using a pre-defined communication protocol (e.g., a IEEE 802.15.4 protocol or a custom or proprietary protocol), either wirelessly or along a wire. The sensor gateway 160 may be configured to receive communications from these sensors that are analog and/or digital in nature.

The environmentally controlled area 140 may include one or more sensors, including a temperature sensor 148, a temperature sensor 150, and a humidity sensor 152. It may be that each of the temperature sensor 148, the temperature sensor 150, and/or the humidity sensor 152 connect to a repeater 162 via one or more wires. It may be that the temperature sensor 148, the temperature sensor 150, and the humidity sensor 152 connect to the repeater 162 wirelessly. In the wired case, it may be that the repeater 162 provides power to one or more of the sensors for the sensors to operate via the wires. These sensors may communicate with the repeater 162 using a pre-defined communication protocol (e.g., a IEEE 802.15.4 protocol or a custom or proprietary protocol), either wirelessly or along a wire. The repeater 162 may be configured to receive communications from these sensors that are analog and/or digital in nature. The repeater 162 may then communicate the information from the temperature sensor 148, temperature sensor 150, and/or humidity sensor 152 to the sensor gateway 160.

It may be that the controller platform 102 can connect to a network 158 via the network interface 110. The network 158 may be, e.g., a network such as a Local Area Network (LAN) or the Internet. Accordingly, the network interface 110 may be compatible with protocols supported by these networks (e.g., a TCP/IP protocol). The network interface 110 may be a wired interface or a wireless interface.

The sensor gateway 160 may also connect to the network 158 to facilitate the communication of sensor data from the sensors 142-152 to the controller platform 102 via the network 158. Accordingly, this may be a wired connection or a wireless connection and may be compatible with various network protocols (e.g., a TCP/IP protocol).

The repeater 162 may connect to the sensor gateway 160 to facilitate the communication of sensor data from the sensors 148-152 to the sensor gateway 160 and onward to the controller platform 102 in the manner described above. Accordingly, this may be a wired or a wireless connection. The repeater 162 may be useful in cases where a placement of the one or more of the sensors 142-152 (e.g., due to the location of the environmentally controlled area 140) is too far away from the sensor gateway 160 to connect directly to the sensor gateway 160. It is also contemplated that a repeater (e.g., the repeater 162) may instead connect to another repeater, which other repeater is connected to either still another repeater or the sensor gateway 160. In this way, a "tree" system may be formed with a single sensor gateway (e.g., the sensor gateway 160) at the top and a hierarchy made up of a plurality of repeaters (e.g., the repeater 162) at various levels beneath the sensor gateway. This may allow for extensibility in the physical range of the system.

It is contemplated that in other embodiments (not illustrated), the sensors 142-152 may connect to the network interface 110 (e.g., via a directly wireless link between each sensor 142-152 and the network interface 110) rather than via, e.g., the sensor gateway 160 and/or the repeater 162 and from there through the network 158. It is contemplated that in still other embodiments, the sensors 142-152 may connect to a device of the network 158 rather than to a sensor gateway 160 and/or a repeater 162. Accordingly, in these embodiments, a sensor gateway 160 and/or a repeater 162 may not be necessary.

It may be that the sensors 142-152, the repeater 162, and the sensor gateway 160 of the system 100 communicate using a Wireless Sensor Network (WSN) between them. This WSN may operate on, for example, an IEEE 802.15.4 protocol. The sensor gateway 160 may be configured to receive data from the sensors 142-152 and/or the repeater 162 on the WSN and forward that data for use on the network 158, which may use a different protocol than the IEEE 802.15.4 protocol (e.g., a TCP/IP protocol).

The processor 104 may use the data collection engine instructions 124 to implement a data collection engine for the controller platform 102 of the system 100. Through the data collection engine, the controller platform 102 may be capable of collecting data (e.g., sensor readings and/or other data, such as configuration data) from the sensors 142-152 via the connections described above. This data may include, for example, temperature readings and/or humidity readings.

A data collection engine of the controller platform 102 may further record over time the readings taken from a given sensor or sensors and store this information in the collected sensor data 118. These data points may be stored in the collected sensor data 118 along with a timestamp provided to the processor 104 either with the collected sensor data 118 and/or by the clock 108. The data points recorded in the collected sensor data 118 may each include one or more of a sensor identifier for the given sensor, a type of data recorded by the sensor, a reading measured by the sensor, and a timestamp applied to the temperature reading by the system at the time the temperature is taken.

In some embodiments disclosed herein, the data collection engine may generate data points for a measured environmental characteristic by recording an average of multiple readings measured by a sensor along with a timestamp associated with a time period during which the multiple readings were taken. Examples of this may be, e.g., a data point corresponding to an "average air temperature." This method of collecting data points may be useful in the case where it is not necessary for the data collection engine to store data points at the same frequency at which sensor readings are taken. It is to be understood that display, analysis, and use of data sets containing data points reflecting these averaged values will be the same as the display analysis and use of sensor data sets containing data using non-averaged data points (e.g., data points directly associating a single sensor reading with a timestamp). Accordingly, discussion of, e.g., a data set with data points gathered by sensor readings should be understood as equally referring to the averaged case and the non-averaged case, as context permits.

A data collection engine of the controller platform 102 according to some embodiments herein may take readings from the sensors in an automated manner. For example, the one or more sensors may be placed at the locations for which the corresponding data (e.g., temperature, humidity) is to be collected. The sensor may then be configured using, e.g., a control engine of the controller platform 102. Once configured, the controller platform 102 may collect and/or store readings from the one or more sensors in the future without further human intervention.

A data collection engine of the controller platform 102 according to some embodiments herein may take and record sensor readings from one or more sensors 142-152 once per time period (e.g., at a given frequency). This time period may change based on the needs of the related use case. For instance, a controller platform 102 may automatically read and record a sensor reading of a sensor 142-152 every second (or even more frequently), or at least every few seconds, when frequent sensor readings may be useful in the given use case. In use cases that do not demand such frequency, a sensor 142-152 may be read, and the result recorded, for example, every minute, every few minutes, or once an hour. Persons with ordinary skill in the art will recognize that a system according to embodiments herein may be configured to take sensor readings of the one or more sensors 142-152 with any frequency necessary to meet the needs of a given use case.

A data collection engine of the controller platform 102 according to some embodiments herein may perform calculations on the collected data points. Examples of such calculations are given in additional detail below. This calculation data may also be stored by the data collection engine in the collected sensor data 118.

In some embodiments disclosed herein, the data collection engine may perform a plurality of such calculations and associate an average of the result with a timestamp corresponding to the underlying data points. An example of this may be a data point corresponding to an "average estimated product temperature." This method of calculating data points may be useful in the case where it is not necessary for the data collection engine to record data points at the same resolution at which sensor readings are taken. It is to be understood that display, analysis, and use of data sets containing data points reflecting these averaged values will be the same as the display analysis and use of sensor data sets containing data using non-averaged data points (e.g., data points directly associating a single calculated value with a timestamp). Accordingly, discussion of, for example, a data set with data points calculated by the data collection engine should be understood as equally referring to the averaged case and the non-averaged case, as context permits.

A data collection engine of the controller platform 102 may be capable of recognizing bad sensor readings and further of marking them as such when it stores them in the collected sensor data 118. The data collection engine may elect not to use sensor readings marked as bad when performing calculations.

The processor 104 may use the display engine instructions 126 to implement a display engine for the controller platform 102 of the system 100. Such a display engine may control and/or interact with a display device 154 of a user of the system 100. A display engine of the controller platform 102 according to embodiments herein may be configured to display collected data points to a user. The display device 154 may be, for example, a device with a screen that is in network communication with the system via the network interface 110. Alternatively, the display device 154 may be a device with a screen that is connected to the controller platform 102 in another manner (such as, e.g., a Video Graphics Array (VGA) cable or High Definition Media Interface (HDMI) cable at the I/O interface 112). In all of these cases, the controller platform 102 may present, via the display engine, collected data points from the collected sensor data 118 (or other information) on the display device 154. The display device 154 may be a personal computer, a smartphone, or any other device capable of being configured to display the collected temperature data points.

The processor 104 may use the control engine instructions 128 to implement a control engine for the controller platform 102 of the system 100. Such a control engine may control the controller platform 102 according to the control commands. A control engine of a controller platform 102 according to embodiments herein may be configured to accept control commands from the user. These control commands may be sent by the user using a control device 156 that is connected to the system (e.g., via the network interface 110 of the controller platform 102). For example, one or more control commands from the control device 156 may determine the range of data points that have been collected that should be displayed or otherwise reported to the user. Control commands from the control device 156 may also be used to configure other settings of the system, for example: a period at which a given temperature sensor should take temperature readings to be recorded by the controller platform 102 (or the period at which the controller platform 102 should take and record a reading from a sensor), whether a given temperature sensor is active and/or powered on, the specific circumstances under which to generate an alert, how to perform an alert, etc. Control commands may also include, for example, creation of a data structure representing a location (e.g., a facility) having one or more sensors gathering data for the system, managing alert notifications sent based on alert conditions at those locations, managing user records (e.g., managing visibility of users, managing authority of users for data viewing and/or system data entry and control, and recording media accounts (email accounts, phone numbers, etc.) at which to notify users of the alerts), computing and displaying a network graph of a gateway and all of its repeaters/sensors along with optionally a signal strength between each of these elements, computing reports for display, etc.

A control engine of a controller platform 102 may further perform other tasks, such as configuring alerting thresholds, maintaining user records, location records for sensors, and schedules (for, e.g., a sensor).

Finally, a control engine of a controller platform 102 may maintain security (e.g., by restricting the display of data and/or the control of the controller platform 102 to users who can authenticate with the control engine).

It is contemplated that in some embodiments, the control device 156 may be the same device as the display device 154 (or it may be a different device).

The processor 104 may use the audit engine instructions 130 to implement an audit engine for the controller platform 102 of the system 100. An audit engine of the controller platform 102 according to embodiments herein may be configured to collect audit data from a user of the controller platform 102. This data may be stored in the memory 106 as user audit data 120. This data may relate to circumstances about data from the collected sensor data 118, and may have been provided by a user of the controller platform 102 or automatically generated by the controller platform 102. The user audit data 120 may include data that is different than the data that the controller platform 102 collects via sensors.

The processor 104 may use the recognition engine instructions 132 to implement a recognition engine for the controller platform 102 of the system 100. A recognition engine of the controller platform 102 according to embodiments herein may be configured to recognize patterns and/or make predictions using, for example, the collected sensor data 118, the user audit data 120, and/or the training data 122.

A recognition engine of a controller platform 102 may sample the collected sensor data 118 to learn the correlation of data found therein to alert outcomes. It may observe data from, e.g., a data collection engine and/or a control engine of the controller platform 102 in order to predict the probability of one or more future data alerts. Examples of the nature and use of these patterns and/or predictions are provided in additional detail below.

The recognition engine may use computer learning methods (e.g., neural network (NN) training) in order to improve its function. Data generated by this computer learning method may be stored in the training data 122 of the controller platform 102.

The processor 104 may use the alerts engine instructions 134 to implement an alerts engine for the controller platform 102 of the system 100. An alerts engine of the controller platform 102 according to embodiments herein may be configured to provide alerts to one or more outside entities based on the collected sensor data 118 (which may include sensor-reading-based calculations made by a data collections engine, as described above) of the controller platform 102, and/or a prediction and/or recognition made by a recognition engine of the controller platform 102. These alerts may be triggered based on one or more settings (e.g., threshold values) that may have been set by a control engine of the controller platform 102. These alerts may be of various types, such as text, voice, email, etc.

The processor 104 may use the validation engine instructions 136 to implement a validation engine. A validation engine of the controller platform 102 according to embodiments herein may be configured to provide validation services, such as the provision of HTTPS service to other devices of the system 100 (e.g., the sensors 142-152 and/or the sensor gateway 160). A validation engine of the controller platform 102 may also be used to validate credentials from incoming devices, (e.g., the sensor 142-152, the sensor gateway 160, the display device 154, and or the control device 156). A validation engine of the controller platform 102 may also be used to ward off DDOS attacks (and may dynamically scale in order to perform this function).

Figure 2:
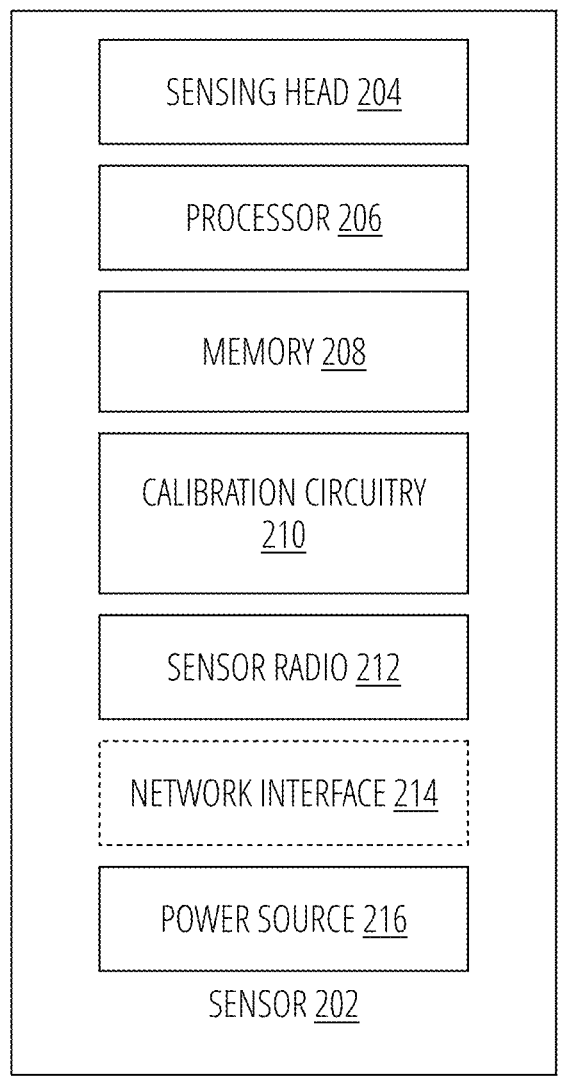
FIG. 2 illustrates a sensor according to some embodiments.

FIG. 2 illustrates a sensor 202 according to some embodiments. The sensor 202 of FIG. 2 may correspond to any one of the temperature sensor 142, the temperature sensor 144, the humidity sensor 146, the temperature sensor 148, the temperature sensor 150, and/or the humidity sensor 152 of the controller platform 102 of FIG. 1. The sensor 202 may include a sensing head 204, a processor 206, a memory 208, calibration circuitry 210, a sensor radio 212, a network interface 214, and a power source 216.

The sensing head 204 of the sensor 202 may be capable of taking a reading of an environmental characteristic (e.g., temperature and/or humidity) around the sensing head 204 and reporting the characteristic to the processor 206 of the sensor 202. The sensing head 204 may be a digital device made to output, for example, a bit pattern corresponding to the reading (e.g., a digital humidity sensor), and/or the sensing head 204 may be an analog device made to output, for example, a certain voltage or current corresponding to the reading (e.g., a thermistor for a temperature reading).

The processor 206 may be able to receive and interpret the output from the sensing head 204 and determine a value corresponding to the output (e.g., via an analog to digital conversion and/or a digital to digital conversion, if necessary). The processor 206 may interface with the sensor radio 212 and/or the network interface 214 in order to communicate these values externally.

The processor 206 may also be capable of encrypting outgoing communications and decrypting communications. The processor 206 may interface with the memory 208 of the sensor 202 in order to fetch instructions for the processor 206 that allow it to perform its functions.

The sensor 202 may also include calibration circuitry 210, which may be used by the processor 206 to calibrate the sensing head 204. This calibration circuitry 210 may include circuitry elements of a known value that the processor 206 can use in conjunction with a signal from the sensing head 204 in order to tune itself to the real-world characteristics of the sensing head 204.

It is contemplated that in some embodiments, the sensor 202 may include multiple sensor heads (e.g., more sensing head(s) than just the sensing head 204). These additional sensing head(s) (e.g., beyond the sensing head 204) may read the same environmental characteristic as the sensing head 204 or a different environmental characteristic. When a sensor (e.g., the sensor 202) with multiple sensing heads is used in this manner, the processor (e.g., processor 206) of the sensor may report as multiple logical sensors to other elements of the systems described herein (e.g., the processor may provide multiple sets of data over time to a controller platform (e.g., the controller platform 102)). Each logical sensor may correspond to one of the multiple sensing heads according to the type and placement of the sensing head. For example, a single sensor with multiple sensing heads may report as, e.g., both the temperature sensor 142 and the temperature sensor 144 of FIG. 1. Further, some or all of the sensing head(s) may be connected to the sensor via a wire, making it possible that the two or more sensing heads of a sensor may each correspond to a different environmentally controlled area. For example, a sensor with multiple sensing heads may report as, e.g., both the temperature sensor 142 and, e.g., a humidity sensor (other than the humidity sensor 152) that has been placed in the environmentally controlled area 140 of FIG. 1. That sensing head(s) may be physically extendible in the manner described also means that a sensor may take readings at a temperature controlled area when, e.g., a sensing head of the sensor (instead of, e.g., the entire sensor) is located within the temperature controlled area. In embodiments described herein, it may be that the placement or location of the sensor (including, e.g., a logical sensor) is considered to as the placement of the corresponding sensing head.

The sensor 202 may further include a sensor radio 212 to communicate data from the processor 206 to an outside entity (e.g., a repeater or a sensor gateway). This communication may be in the form of a digital signal or an analog signal corresponding to the needs of the receiving outside entity and as provided by the processor 206. The sensor radio 212 of the sensor 202 may communicate with the outside entity using a pre-defined communication protocol (e.g., a IEEE 802.15.4 protocol or a custom or proprietary protocol). It may be that the sensor radio 212 operates on a WSN that includes a sensor gateway and possibly one or more repeaters, as described above.

It is contemplated that in some embodiments, the sensor 202 may include a network interface 214. The network interface 214 of the sensor 202 may be capable of communicating with, for example, the network interface 110 of the controller platform 102 directly and/or via equipment found in the network 158. In either case, it may not be necessary for the sensor 202 in these cases to use the sensor radio 212 to communicate with, for example, the sensor gateway 160 (or similar, such as a repeater) in order to interface with the network 158. In these embodiments, the network interface 214 may connect to the network 158 and/or the controller platform 102 via one or more wires (e.g., Ethernet cables). Alternatively (or additionally), the sensor network interface 214 may connect to the network 158 and/or the controller platform 102 wirelessly (e.g., the network interface 214 may be a 5G compatible interface). In each case, the network interface 214 of the sensor 202 may communicate with the network interface 110 of the controller platform 102 (either directly or through the network 158) using a pre-defined communication protocol (e.g., an IEEE 802.11 protocol, or a 5G protocol).

The sensor 202 may further include a power source 216. The power source 216 may provide the sensor 202 the power to operate. The power source 216 may be, for example, a battery found on the sensor 202. Alternatively, the power source 216 may be a wired connection to an external power source.

Figure 3:
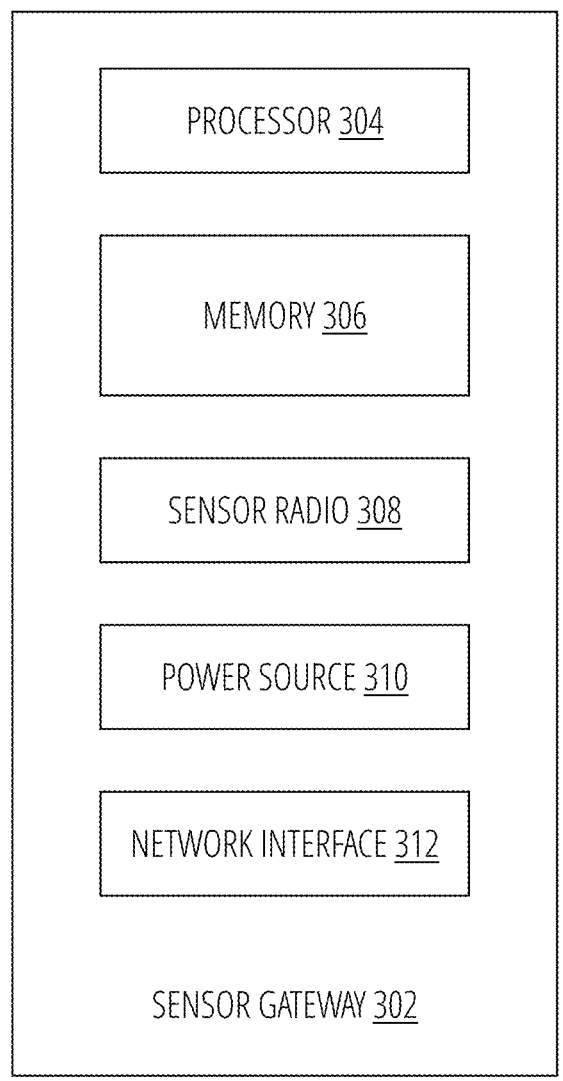
FIG. 3 illustrates a sensor gateway according to some embodiments.

FIG. 3 illustrates a sensor gateway 302 according to some embodiments. The sensor gateway 302 may correspond to the sensor gateway 160 of FIG. 1. The sensor gateway 302 may include a processor 304, a memory 306, a sensor radio 308, a power source 310, and a network interface 312.

The processor 304 may interface with the sensor radio 308 to communicate with a sensor (e.g., one of the sensors 142-152 of FIG. 1). This communication may include receiving data from a sensor and/or sending control signals to a sensor. It may be that the sensor radio 308 operates on a WSN that includes a sensor gateway and possibly one or more repeaters, as described above. The processor 304 may also interface with the network interface 312 in order to communicate with a controller platform (e.g., the controller platform 102 of FIG. 1). This communication may include sending data from a sensor to the controller platform and/or receiving control commands for the sensor gateway 302 and/or a sensor in communication with the sensor gateway 302 via the sensor radio 308. The sensor gateway 302 may be configured to receive data on the sensor radio 308 according to one protocol (e.g., a IEEE 802.15.4 protocol or a custom or proprietary protocol) and send data on the network interface 312 according to a second protocol (e.g., a IEEE 802.11 protocol). The processor 304 may perform these communications via the sensor radio 308 using, for example, an IEEE 802.15.4 protocol or a custom or proprietary protocol.

The processor 304 may be capable of encrypting all outgoing communications and decrypting incoming communications. The processor 304 may interface with the memory 306 of the sensor gateway 302 in order to fetch instructions for the processor 304 that allow it to perform its functions.

The sensor gateway 302 may further include a power source 310. The power source 310 may provide the sensor gateway 302 the power to operate. The power source 310 may be, for example, a battery found on the sensor gateway 302. Alternatively, the power source 310 may be a wired connection to an external power source.

Figure 4:
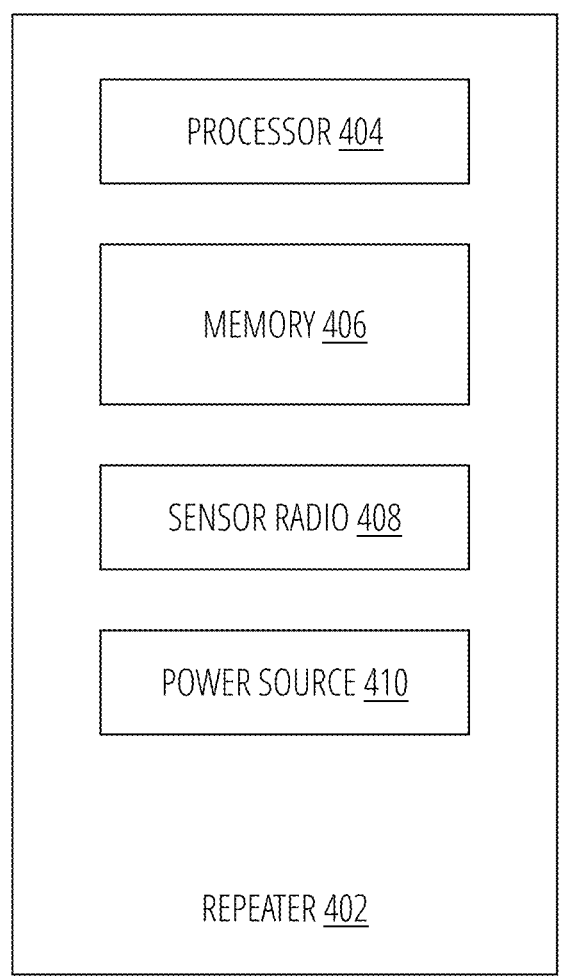
FIG. 4 illustrates a repeater according to some embodiments.

FIG. 4 illustrates a repeater 402 according to some embodiments. The repeater 402 may include a processor 404, a memory 406, a sensor radio 408, and a power source 410.

The processor 404 may interface with the sensor radio 408 to communicate with a sensor (e.g., one of the sensors 142-152 of FIG. 1). This communication may include receiving data from a sensor and/or sending control signals to a sensor. The processor 404 may also interface with the sensor radio 408 to communicate with a sensor gateway (e.g., the sensor gateway 160 of FIG. 1) in order to ultimately communicate sensor data between a sensor (e.g., the sensors 142-152 of FIG. 1) and a controller platform (e.g., the controller platform 102 of FIG. 1). This communication may include sending data from a sensor to the sensor gateway and/or receiving control commands for the repeater 402 and/or a sensor in communication with the repeater 402 from a sensor gateway via the sensor radio 408. It may be that the sensor radio 408 operates on a WSN that includes a sensor gateway and possibly one or more sensors, as described above. The processor 404 may also interface with the sensor radio 408 to communicate with another repeater in order to ultimately communicate sensor data provided by that other repeater to a sensor gateway.

The processor 404 may be capable of encrypting all outgoing communications and decrypting incoming messages. The processor 404 may interface with the memory 406 of the repeater 402 in order to fetch instructions for the processor 404 that allow it to perform its functions.

The repeater 402 may further include a power source 410. The power source 410 may provide the repeater 402 the power to operate. The power source 410 may be, for example, a battery found on the repeater 402. Alternatively, the power source 410 may be a wired connection to an external power source.

Figure 5:
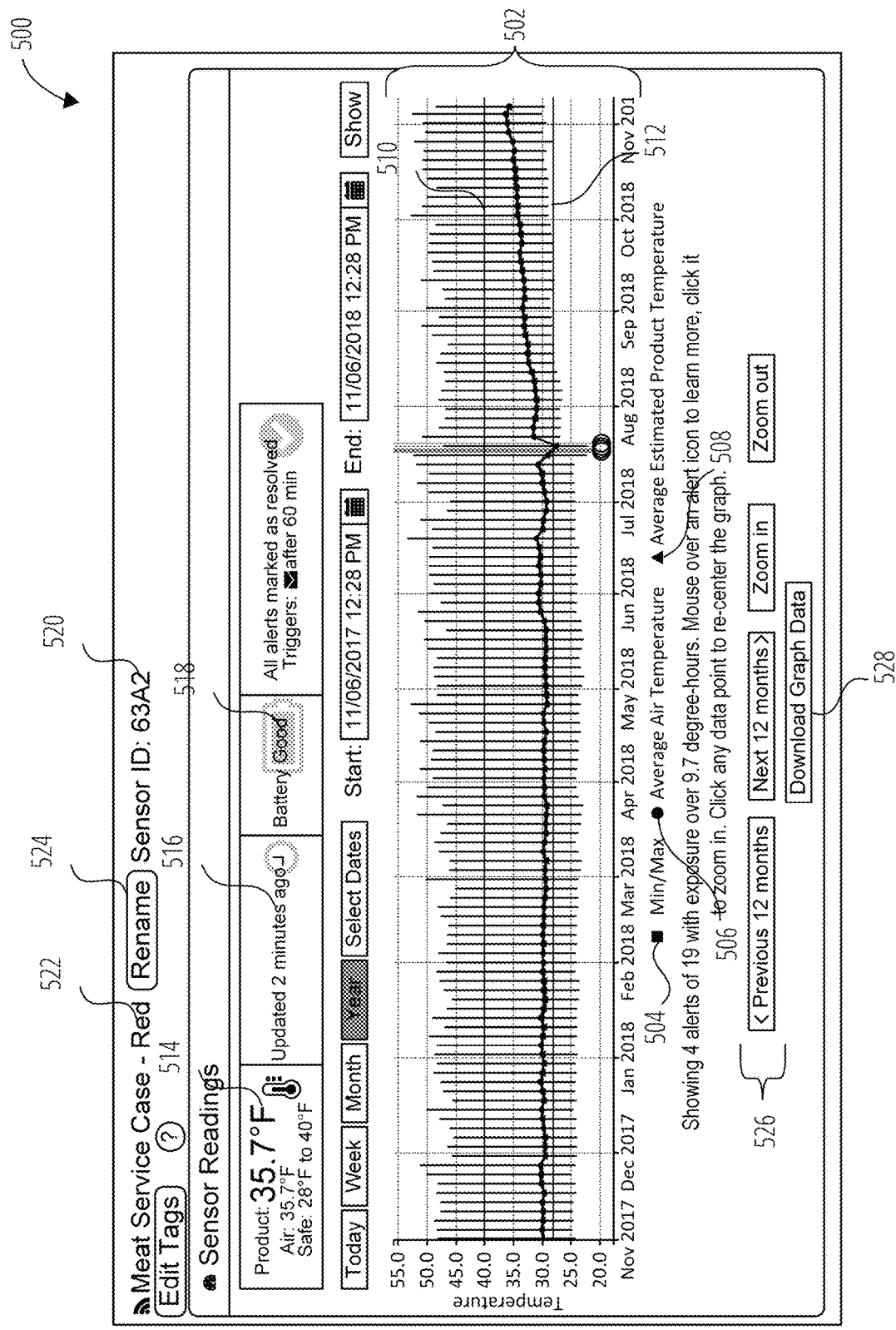
FIG. 5 illustrates an example of a display of a long period of temperature-related data over time, according to some embodiments.

FIG. 5 illustrates an example of a display 500 of a long period of temperature-related data over time, according to some embodiments. The display 500 may have been drawn on a screen of a display device by a display engine of a controller platform, as described above. The display 500 may correspond to a sensor that is in communication with the controller platform, as described above.

The display 500 may include a data region 502. The data region 502 may include all or a portion of the data detected by/corresponding to a sensor, which may include, for example, vertical min/max temperature bars 504 corresponding to a sub-period of the data region 502, an average air temperature 506 corresponding to a sub-period of the data region 502, and/or an average estimated product temperature 508 corresponding to a sub-period of the data region 502. The data region 502 may also reflect an upper threshold 510 and/or a lower threshold 512 corresponding to the sensor, each of which may have been set by the user (further discussed below).

In the embodiment of FIG. 5, it may be that the period of time represented is a year long. One benefit of long-term data display is that it may allow the user to more readily identify relatively smaller, yet significant, migrations from a long-term mean. For example, a year-long view of a temperature sensor in, e.g., a refrigerator in a restaurant may illustrate a span of time where average temperatures measured by one or more temperature sensors are higher than the mean. This would allow a user to investigate the circumstances that are causing this acute change in average temperature (such as, e.g., a new employee not consistently shutting a refrigerator door during a given period of time).

The display 500 may also include a current sensor reading 514 of the sensor, an update information 516 describing the last time the current sensor reading 514 was updated, and/or a battery information 518 indicating the status of the battery of the sensor (if the sensor is battery powered).

The display 500 may also include a sensor ID 520 for the sensor from which the data was collected. This ID may be a system-wide ID for the sensor that is used by elements in the system (e.g., the controller platform) to consistently identify the sensor. This sensor ID 520 may be, e.g., some or all of a network address (e.g., a radio MAC address) of the sensor.

The display 500 may also include a sensor name 522 of the sensor. This sensor name 522 may be set by the user such that a human reading the name has some contextual information about the sensor's location (e.g., the use of "Meat Service Case—Red" as illustrated may alert the user that the sensor is in a meat service case). The sensor name 522 may be able to be changed by the user through using the rename button 524.

The display 500 may also include date control elements 526. The date control elements 526 may allow the user to control the length and amount of time for which the data region 502 displays the data. The date control elements 526 may include buttons, sliders, menus, calendars, etc., all of which may allow the user to set the beginning and end of the data region 502 as to time.

The display 500 may include a download button 528. The download button 528 may allow the user to download the data that is currently displayed in the data region 502. It may also allow the user to download all (or some other subset of) the data for the sensor (whether or not the current display 500 shows such data).

Each of the user input features relative to the display 500 discussed herein may implement their described changes via a control engine of a controller platform, in the manner described above.

Another benefit of long-term data display is that it may be that a long-term trend is more recognizable to a user when a graph over a long period of time is available to the user. Depending on various circumstances, it is possible that the environmental characteristic being measured by a given sensor is slowly changing over time. This may occur when, for example, a refrigerator with a temperature being measured by a temperature sensor is becoming blocked up by ice or has a slow refrigeration leak. The display of a long period of temperature data over time may alert the user that some long-term problem may be occurring, allowing the user to investigate the problem before any goods that depend on proper temperatures are lost.

Figure 6:
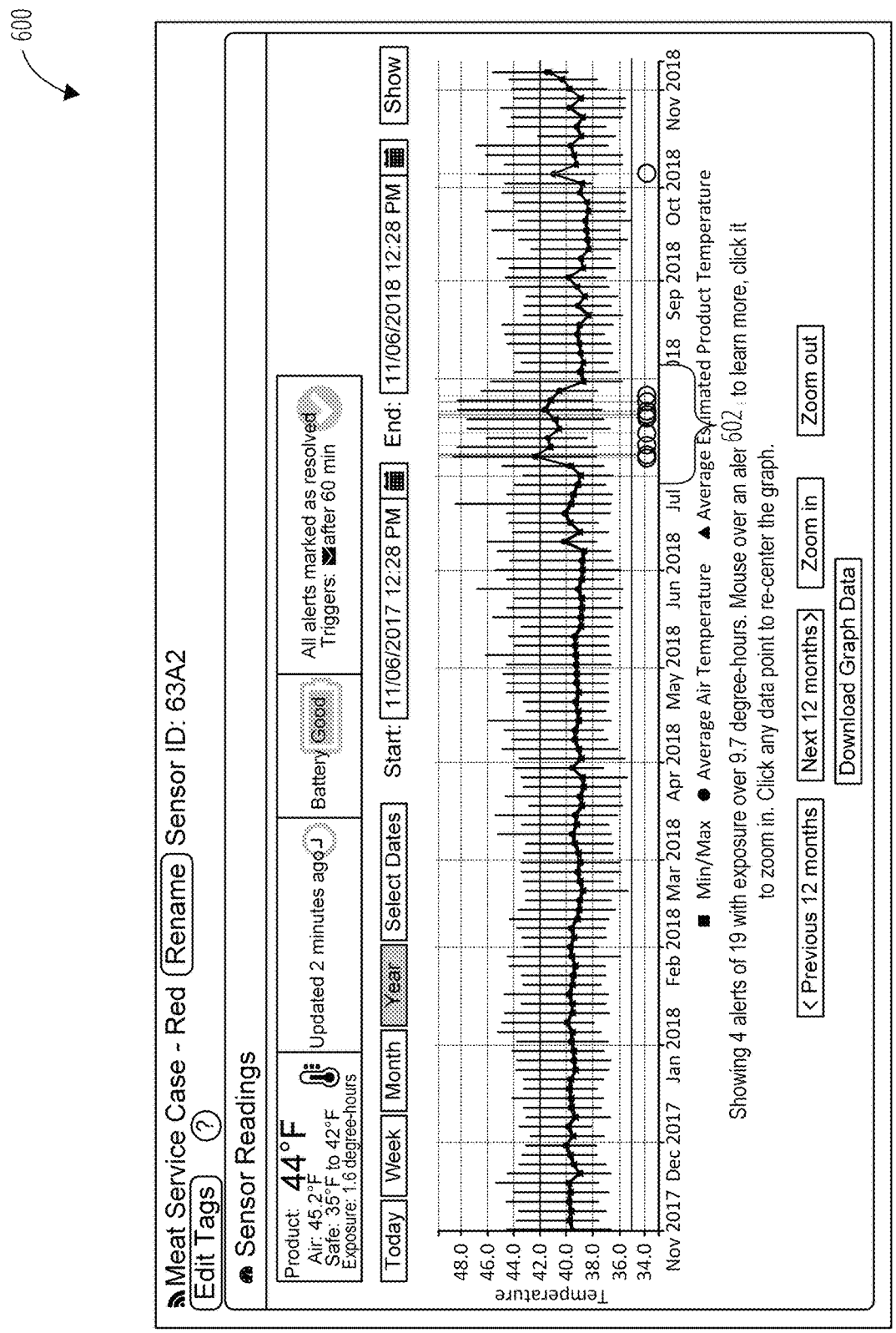
FIG. 6 illustrates an example of a display of a long period of temperature-related data over time, according to some embodiments.

FIG. 6 illustrates an example of a display 600 of a long period of temperature-related data over time, according to some embodiments. Elements of FIG. 6 may include those elements described in relation to FIG. 5 above.

FIG. 6 illustrates that for a period 602 of about a month, the data (which may correspond to sensed temperature) was unusually high as a historical matter (e.g., in comparison to previous data). A user viewing this data would have been able to notice this at the time and would have been able to investigate to determine whether one of the issues presented above (or another issue) was present at the location.

It may be that the availability of long-term environmental data helps the user be aware of these or other long-term trends that are indicative of a pending failure of environmental control (e.g., an impending failure in a refrigerator holding the goods). Awareness of pending environmental control failures may help a user of a system according to present embodiments to protect the goods monitored by the system from spoliation by becoming aware of and performing needed maintenance. Further, this increased ability to schedule maintenance prior to environmental control failure avoids the need for off hours or no-notice service calls, dramatically reducing maintenance costs.

A system according to embodiments herein may be configured to perform additional calculations on the collected environmental data points. Such calculations may be performed using, for example, a data collection engine of a controller platform of the system, as described above.

For example, in cases where the ambient temperature of an area where a good stored is being measured by one or more sensors of the system, the data collection engine of the system may be configured to use mathematical methods and/or formulae to calculate the temperature the of good itself. These methods may use, e.g., Newton's law of cooling (or other methods) in order to estimate the actual temperature of the good over time relative to the ambient temperature of the corresponding storage area over time. Calculations using Newton's law of cooling may use the formula:

$$T(t) = T_s + (T_o - T_s) * e^{-kt}$$

In this formula, t is the time, T(t) is the temperature of the good at time t, $T_s$ is the surrounding temperature (e.g., the air temperature detected by a sensor of the system), $T_o$ is the initial temperature of the good, and k is a constant. The constant k may be a constant corresponding to the heat transfer characteristics of a good being used in the controlled environment corresponding to the sensor. The constant k may alternatively be a constant that is good enough to act as such a constant for a variety of one or more goods of a same loosely defined type. The constant k may be provided to the system by the user, who may be aware of an appropriate constant to use in relation to the good being measured (e.g., via experimentation or via the vendor of the system).

The temperature of the good over time may be stored by the data collection engine of the system. In some embodiments, this information may be stored in the collected sensor data of a data store of a controller platform. This information may be stored with a timestamp that is the same as the timestamp associated with the sensor reading that was used in the formula (e.g., the same timestamp associated with the $T_s$ parameter).

The data collection engine of the system may also calculate Nth order derivatives of the collected temperature data and/or the temperature of the good over time as well, which may also be stored as collected sensor data. For example a first order derivative of the temperature data over time may provide the rate of change at one or more points in time of the temperature data. As another example, a second order derivative of the temperature of the good over time may provide the rate of acceleration of the rate of change of the temperature of the good over time. This data may be stored as collected sensor data as well. This data may be used by, for example, a recognition engine of the system in computer learning/prediction processes (described below).

Once the temperature of the one or more goods has been estimated over time, one or more mathematical methods can be used in order to estimate a level of exposure to bacterial growth (or other cause of temperature-related spoliation, such as temperature-related deterioration) that has occurred at the good relative to the changes in temperature of the good over time. For example, the data collection engine of the system may calculate (or be provided by, e.g., a user) a temperature threshold for a given good. The data collection engine of the system may then be configured to determine the presence and/or an amount of, e.g., bacterial growth taking place within the good once it is determined that the temperature of the good has exceeded the threshold. A level of exposure may be determined (at least in part) by using the amount of time that the estimated temperature of the good has been outside the given threshold amount. The level of exposure may also be determined (at least in part) by using the amount over which the temperature of the good has surpassed the threshold amount. The measured level of exposure may be calculated over the life of the good, or it may be measured over smaller time periods.

One way calculating a level of exposure is to calculate a degree-hours value for exposure relative to the good being monitored. For example, if it is determined that a good spent five hours at 1 degree over the given threshold, it may be determined that the good suffered 5 degree-hours of exposure. As another example, if it is determined that a good spent one hour at 5 degrees over the threshold, it may also be determined that the good suffered 5 degree-hours of exposure. As a third example, if it is determined that the good spent one-half hour at 7 degrees over the threshold, it may be determined that the good suffered 3.5 degree-hours of exposure.

Figure 7:
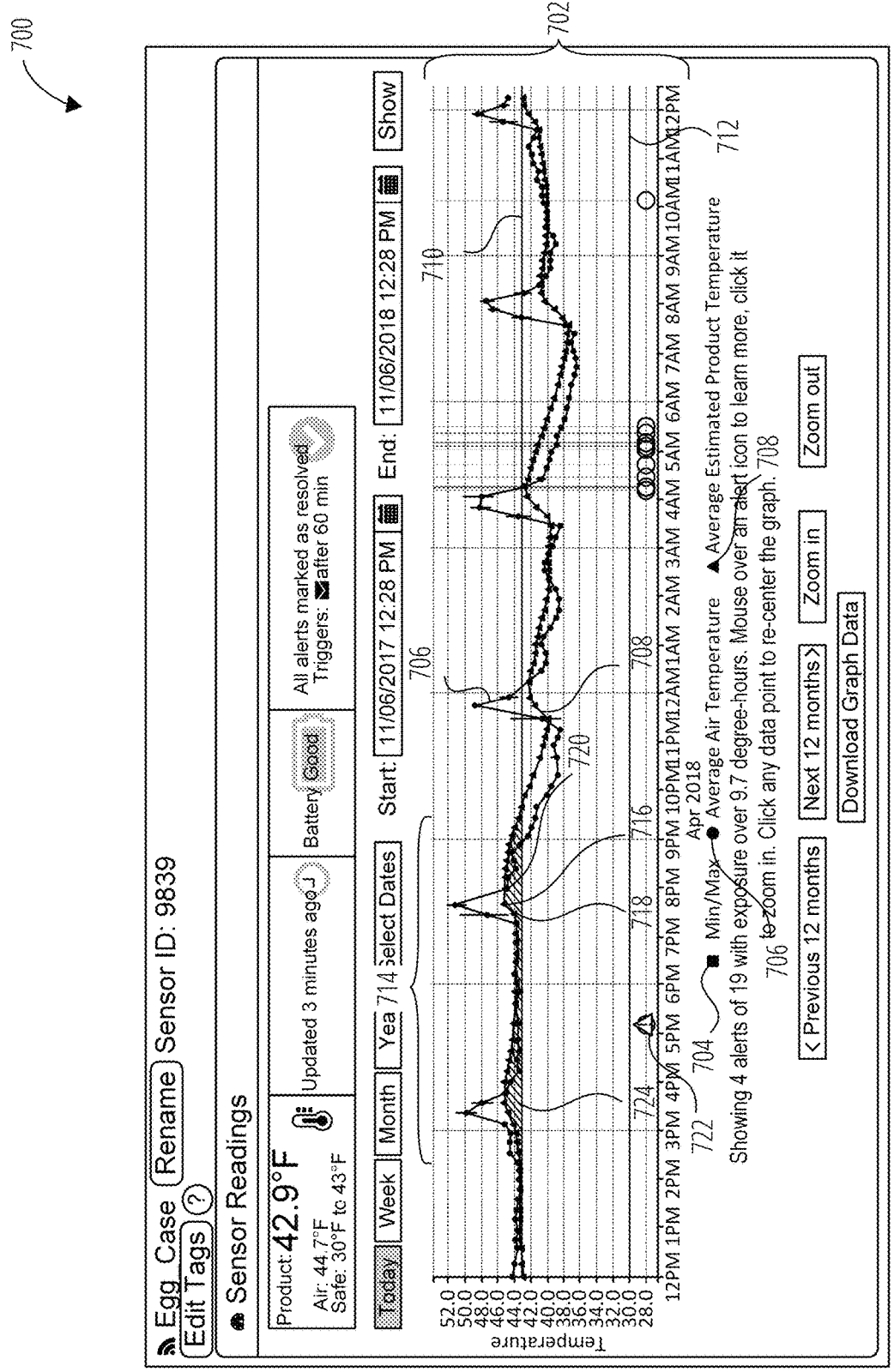
FIG. 7 illustrates an example of a display corresponding to the use of a degree-hour calculation for exposure.

FIG. 7 illustrates an example of a display 700 corresponding to the use of a degree-hour calculation for exposure. The display 700 may be similar to the display 500 that was discussed in relation to FIG. 5 above. The display 700 may include a data region 702 that includes data. The data may include, for example, vertical min/max temperature bars 704, an average air temperature 706, and/or the average estimated product temperature 708. The data region 702 may further indicate an upper threshold 710 and a lower threshold 712, which may have been set by the user.

The data collection engine of the system may have detected the average air temperature 706 and subsequently used this to calculate the average estimated product temperature 708 data in the manner described above. As indicated by the average estimated product temperature 708 data, it may be that the temperature of the product may have been above the upper threshold 710 (41 degrees) during an exposure period 714. In order to calculate an overall exposure in degree-hours, the data collection engine of the system may take a timestamp of a data point 716 of the average estimated product temperature 708 within the exposure period 714 and subtract from that value the timestamp of a previous data point 718. It may then multiply this value by the difference between the upper threshold 710 and the temperature value of the data point 716. This process may be repeated for each data point in the exposure period 714. The values resulting from this process (across all data points for the average estimated product temperature 708 corresponding to the exposure period 714) may then be summed together to reach an overall degree-hour value for total exposure over the exposure period 714.

Accordingly, the calculated exposure value for the exposure period 714 may correspond to the area 724 between the upper threshold 710 and the average estimated product temperature 708 during the exposure period 714. It is further contemplated that this process may be continuously performed while the data is still being collected corresponding to the exposure period 714, and that the exposure value corresponding to the part of the exposure period 714 that is determinable at a given time may be continuously updated according to any new incoming data. Further, the calculated exposure corresponding to all or part exposure period 714 may then at any time be added to any previous calculated exposure (e.g., corresponding to a prior exposure period, not shown) if such previous calculated exposure exists. At any time that any individual or joint exposure value as described above exceeds a set point, an alert 722 may be sent to the user (this is discussed in more detail below).

In some embodiments, it is contemplated that they above method is used but wherein the (absolute value of the) difference between the timestamp of the data point 716 and a subsequent data point is substituted for the difference between the timestamp of the data point 716 of and the previous data point 718.

While this process has been described relative to data points visible in the display 700, it is contemplated that this process may be used across all data points with timestamps corresponding to the exposure period 714 that are stored by the data collection engine of the system (e.g., in a collected sensor data element of a data store, as described above), whether or not they are actually displayed in a given view of the display 700.

While the above description has dealt with exposure relative to product temperatures exceeding the upper threshold 710, it is contemplated that an exposure relative to product temperatures dipping below the lower threshold 712 could be calculated (and reacted to) using analogous methods.

The data collection engine of the system may associate overall degree-hours of exposure at a given point in time with a point in time corresponding to a point at which an estimated product temperature was taken. This data may be stored in the collected sensor data of the system. The data collection engine of the system may calculate Nth order derivatives of this collected exposure data over time as well, which may also be stored as collected sensor data. For example, a first order derivative of the exposure data over time may provide the rate of change at one or more points in time of the exposure. This data may be used by, for example, a recognition engine of the system in computer learning/prediction processes (described below).

Other methods (other than the described degree-hours method) may be used to calculate a level of exposure for a given good. These methods may recognize the non-linear nature of bacterial growth (or other non-linear cause of spoliation, such as temperature-related deterioration) in the good as a function of the temperature of the good. For example, it may be recognized that a good that has been at five degrees over a temperature threshold for one hour may have experienced a different amount of bacterial growth (or other deterioration) than a good that has been at 1 degree over the temperature threshold for five hours.

Non-linear calculations of exposure may make use of or be based upon non-linear methods for calculating bacterial growth and/or growth rates. One such method may use the formula:

$$\mu_m = [b^*(T-T_{min})]^2 \{1-\exp[c^*(T-T_{max})]\}$$

This formula combines the non-linear bacteria growth at any single "danger zone" temperature and adds the complexity of the temperature changing in time. This is a modified version of a model described in D. A. Ratkowsky, et al., 154 Journal of Bacteriology 1222 (1983) that is effective at predicting bacteria growth rates in food, particularly at temperatures near the low point where growth is first observed, which is the area of concern when trying to provide early warning of problems with commercial refrigeration. In the formula above, T is the current temperature in degrees K, $T_{min}$ is minimum temperature where a given strain of bacteria starts to grow in degrees K, $T_{max}$ is the maximum temperature where the bacteria will grow in degrees K, b is the regression coefficient of the square root of growth rate constant r for a particular strain of bacteria versus degrees K for temperatures below the optimal temperature, and c is an additional parameter to enable the model to fit the data for temperatures above the optimal temperature.

Knowing the growth rate at a product temperature T over a finite time period t, total bacteria population can be sufficiently approximated as the collective sum of the growth rate at T* the time t between sensor readings.

Alternatively, the growth rate calculated by the above formula may be used in equations to calculate a total bacteria population in a good in a non-linear manner. For example, once $\mu_m$ is calculated using the formula above, overall bacteria population may be calculated by:

$$y = A\exp\left\{-\exp\left[\frac{\mu_m \cdot e}{A}(\lambda - t) + 1\right]\right\}$$

which is a version of a modified Gompertz equation described in M. H. Zwietering, et al, *Modeling of the Bacterial Growth Curve*, 56 Applied and Environmental Microbiology 1875 (1990). In the formula above, λ is the lag time of bacterial growth, A is the top value possible for bacterial population size expressed in logarithmic terms, $$A = \ln(N_\infty/N_0)$$

where $N_\infty$ is the maximum possible population size and $N_0$ is the initial population of bacteria, and $\mu_m$ is the maximum growth rate of the bacteria (which may have been calculated using the method described above). As described in Zwietering, et al., y may describe in logarithmic terms the relative population growth over time, with $$y = \ln(N/N_0)$$

where N is the population size at time t and $N_0$ is the initial population of bacteria.

Non-linear methods for calculating exposure using these formulas may then consider either or both of the calculated bacterial growth rate and/or the overall calculated bacterial growth (that was determined based on this calculated growth rate) in order to determine an exposure level of a good. An embodiment of exposure-based alert triggering (discussed below) may calculate the worst-case population of common food-based bacterial (or other) contaminants by starting with a given set of initial criteria and comparing an exposure calculation to this population as it relates to widely agreed upon toxic levels by the United States Food and Drug Administration and other world food safety bodies. An embodiment may include alerting when a certain percentage of worst-case toxin population calculation is reached, or the projected time to a critical population is projected and some threshold of time prior to that is reached. The population of bacteria can be calculated, by computing where on the natural growth curve a population is in a perishable good.

A data collection engine of a system according to embodiments herein may associate overall bacterial population at a given point in time with a point in time corresponding to a point at which an estimated product temperature was taken. This data may be stored in the collected sensor data of the system. The data collection engine of the system may calculate Nth order derivatives of this collected bacterial population data over time as well, which may also be stored as collected sensor data. For example, a first order derivative of the exposure data over time may provide the rate of change at one or more points in time of the bacterial population. This data may be used by, for example, a recognition engine of the system in computer learning/prediction processes (described below).

Exposure data (whether, e.g., degree-hours exposure data and/or bacterial population size exposure data, or another type) may be stored by a data collection engine of a system according to embodiments herein. In some embodiments, this exposure data may be stored in the collected sensor data of a data store of a controller platform.

While calculations relative to temperature data have been described in detail above, it is contemplated that analogous calculations may be used relative to other environmental characteristics (such as, e.g., humidity).

A system according to embodiments herein may further be configured to send one or more alerts to one or more users when one or more data points (such as a temperature reading, a humidity reading, a calculated temperature level of one or more goods, and/or a calculated exposure level for one or more goods) is outside of certain boundaries. An alert may be indicated on a display rendered by a user interface, as described herein. Further, the alert may also be communicated to one or more users in the form of one or more phone calls, emails, text messages, or any other alert form directed to getting relatively immediate attention to one or more persons interested in the current environmental characteristics being measured by the one or more sensors. These alerts may be performed by an alerts engine of a controller platform of a system, according to embodiments discussed herein. These alerts may be sent via, for example, a network with which the controller platform communicates via a network interface (e.g., the Internet or a cellular network).

In some embodiments, an alerts engine of a system according to embodiments herein may be configured to send one or more alerts immediately when a sensor reports that an environmental characteristic (e.g., a temperature and/or a humidity) is outside of a given threshold. Other embodiments of the alerts engine of the system may be configured to wait a pre-determined period of time before sending an alert to see whether the environmental characteristic reported by the sensor will return to the given range. An alert may be based on the reading(s) of a single sensor, or an alert may instead be configured to be sent based on the readings of multiple sensors (for example, an alert that is sent when multiple temperature sensors in different, e.g., refrigerators report temperatures outside the range, pointing to a possible power outage or other problem affecting each of the multiple refrigerators).

In place of (or in addition to) alerts sent relative to direct sensor measurements, an alerts engine of the system according to embodiments herein may be configured to alert a user when, for example, a calculated temperature of a good or goods has met or surpassed a certain threshold. For example, the alerts engine may be configured not to alert when a temperature reading is above a certain threshold when it is determined that the estimated temperature of the associated good being monitored is still within the appropriate temperature range (and thus is not receiving exposure). This may be because it is expected or even desirable for the temperature of a container holding a good to fluctuate. For example, it may be necessary to cycle a refrigerated egg case on and off in order to prevent ice buildup on the egg refrigeration equipment and/or to allow for the removal of such ice buildup. In this example, an alerts engine may be configured to alert when the estimated temperature of the eggs, and not the measured temperature reading of the case sensor itself, passes a given threshold.

In other embodiments, an alerts engine of the system may be configured to send an alert when a certain level of exposure has been calculated relative to one or more goods, rather than an alert based purely on a temperature reading of a sensor or a calculated temperature of a good. The alerts engine may begin to send alerts once the level of exposure (however measured) of one or more goods has been calculated to reach a certain level. It may be, for instance, that some low values of exposure do not rise to the level of needing to be reported to the user, and thus the level that the calculated exposure need meet or surpass before the alerts engine is configured to alert a user may be a value above zero. The restriction of alerts until a certain exposure value is reached may therefore act to prevent unnecessary alerts being issued by the alerts engine. Exposure thresholds for alerting purposes may be relative to exposure calculations for a single continuous period of time which the product temperature was outside the safe range. Alternatively, exposure thresholds may be relative to summed exposure calculations relative to multiple (or all) such continuous periods.

An example may involve, e.g., a refrigerator in a grocery store or restaurant. It might be expected that a temperature inside the refrigerator might fluctuate during business hours as customers and/or employees open the refrigerator in order to retrieve goods. The alerts engine of the system may therefore be configured not to alert based on a measured temperature directly (which may lead to constant alerting when the refrigerator is in heavy use), but rather to alert based on a calculated exposure level of the goods in the refrigerator.

Further embodiments of an alerts engine of a system according to embodiments herein may also be configured to change alert trigger characteristics based on an outside context. For example, during business hours, the alerts engine may use an exposure alert trigger characteristic for sending alerts for a sensor in a walk-in refrigerator that is expected to be used during business hours (where it might be anticipated that the temperature of the refrigerator may occasionally and briefly be outside the threshold). However, outside of business hours (when there is no reason the temperature level of the refrigerator should be outside the threshold), the alerts engine may send an alert immediately upon a sensor of a refrigerator crossing a temperature threshold when the threshold is crossed. The details of these contextual considerations may be set by a user of the system, or they may be applied by the system after a NN has inferred these various contexts from, for example, training data of the system (discussed in more detail below).

The reception of an alert may allow a user receiving the alert to respond to the condition that caused the alert. In many cases, a quick response by the user to the condition may be preferred, because there may be a "golden hour" (or other period of time) for which a user response to the condition that caused the alert may be timely enough to mitigate loss of one or more goods due to the alert condition. This means that in many cases, an alerts engine may be configured to send alerts as early as possible after data read or calculated at the system indicates the possibility of a condition that may lead to the damage of one or more goods.

Further, some embodiments of an alerts engine of the system may change the number, recipient(s), and/or type of alert(s) based on the seriousness of the issue. For example, once a calculated temperature level for a given good or goods has met or surpassed a certain (lower) level, some embodiments of the alerts engine may send a single alert (or just a few alerts) to one person (or just a few people). The alert(s) may be in the form of email(s), phone call(s), text message(s), or other alert form(s) (either alone or in combination) to one or more persons who are on-site. On the other hand, once another (higher) calculated temperature level for a given good or goods is met or surpassed, some embodiments of the alerts engine may be configured to send one or more (and/or more frequent) alert(s) to interested persons other than just those persons who are on-site. These alerts may be in the form of higher priority email(s), phone call(s), text message(s), or other alert form(s) (either alone or in combination) that are designed to receive more immediate attention than the alerting methods perhaps used in relation to the lower temperature threshold case.

Various calculated levels of exposure may also be used as triggers for alerts in systems according to embodiments herein. For example, once a certain (lower) level of exposure has been calculated for a given good or goods, some embodiments of an alerts engine of the system may send a single alert (or just a few alerts) to one person (or just a few people). The alert(s) may be in the form of email(s), phone call(s), text message(s), or other alert form(s) (either alone or in combination) to one or more persons who are on-site. On the other hand, once another (higher) level of exposure has been calculated for a given good or goods, some embodiments of the alerts engine may be configured to send more (and/or more frequent) alerts to interested persons other than just those persons who are on-site. These alert(s) may be in the form of higher priority email(s), phone call(s), text message(s), or other alert form(s) (either alone or in combination) that are designed to receive more immediate attention than the alerting methods perhaps used in the lower exposure threshold case.

A division between higher and lower priority levels is also possible when alerting based on directly measured temperature levels at one or more sensors. Further, while preceding disclosure has discussed alerting based on exceeding one or more upper thresholds, it is contemplated that analogous alerting could occur when sensor data and/or calculated data falls beneath one or more lower thresholds.

An alerts engine of the system may be capable of assigning responsibility for an alert generated by an alerts engine. For example, the alerts engine may generate a temperature-based, exposure-based, humidity-based, or other alert and attempt to communicate with a user or group of users using phone calls, emails, text messages, or another alert form, as described above. The alerts engine may be configured to recognize that a communication has been successful (e.g., that a user has picked up a telephone call, or responded to an email or text message). The alerts engine may then assign the user responding to the successful communication as a responsible party for addressing the alert. The assignment of the user as a responsible party may be automatic upon successful communication, or the assignment may occur after the user affirmatively accepts responsibility via the communication method (e.g., by using voice methods to confirm the responsibility assignment or by responding to a text message in a certain way to confirm the responsibility assignment). The assignment of responsibility to a particular user may be saved in the system (with additional data, such as a time stamp, the method of communication used, and/or a record of the communication that led to the assignment of responsibility to the user) for later review (e.g., in user audit data of the system).

The user for which the responsibility is to be assigned may be identified by an alerts engine of the system automatically, using methods such as voice recognition (for a telephone call), or by looking up the user who would normally receive such successful communications on that particular communication channel (e.g., by looking up the user associated with the phone number from which a responsive text message was received). Alternatively, the user to which the responsibility is to be assigned may self-identify.

Once responsibility has been successfully assigned, the alerts engine may cease the alert escalation methods as between different levels of alerts (as discussed herein) for the issue that is generating the alerts in question.

The user or group of users to which any alert described herein may be sent may change based on parameters outside of the configurations of the alerts engine of the system. For example, it may be that an alert during normal business hours will be sent to a single user or to a group consisting of a few people normally expected to be in the store during business hours. It may further be that a similar alert occurring during off-business hours (e.g., at night) will be sent to a larger group of people, or a group of people that has been specially designated to be contacted during off-business hours. Other outside parameters upon which this change may include, but not be limited to, day of the week, month of the year, or another outside parameter that the system has been configured to recognize.

Figure 8:
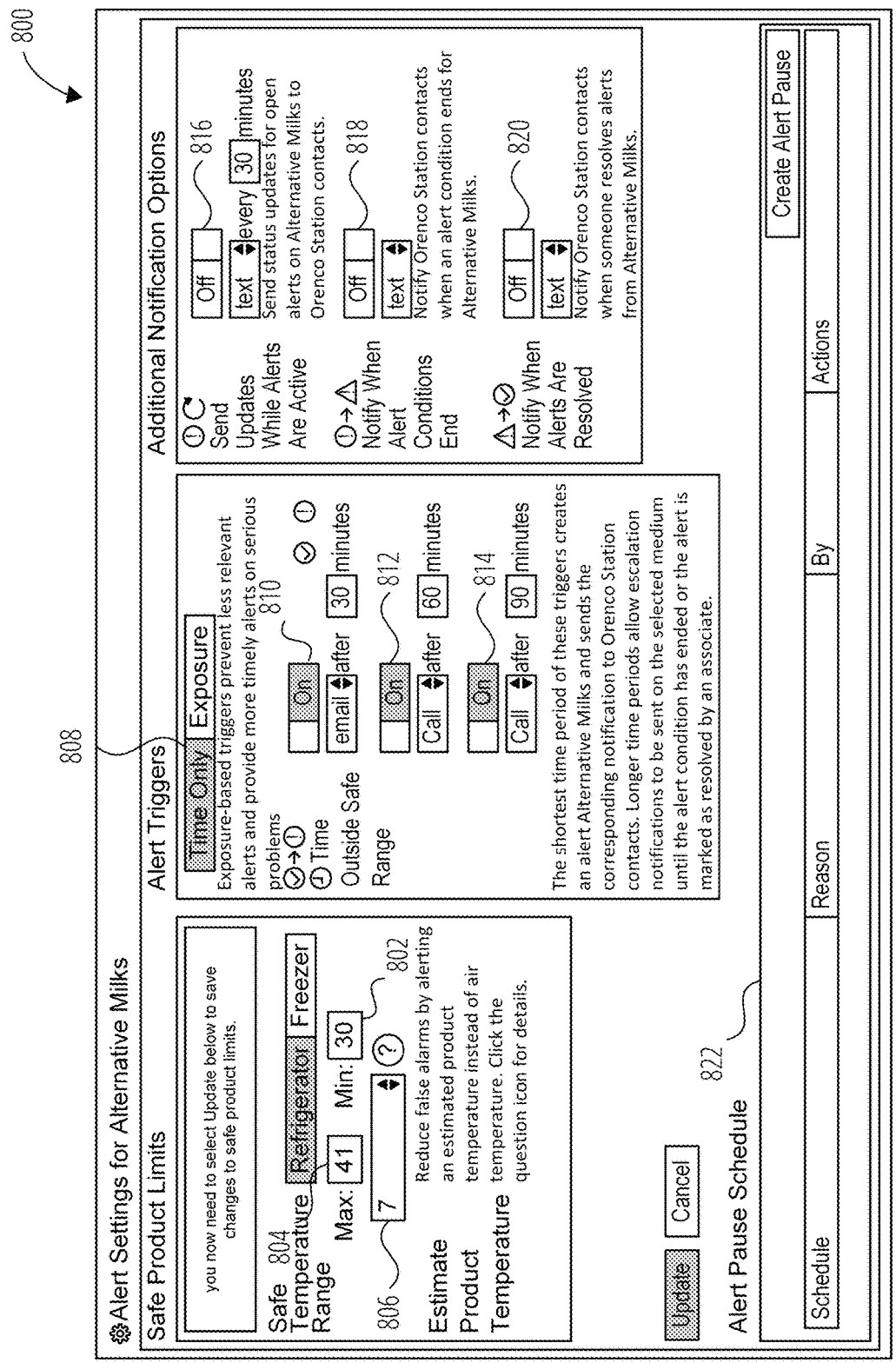
FIG. 8 illustrates a display for configuring alert parameters for a sensor, according to embodiments discussed herein.

FIG. 8 illustrates a display 800 for configuring alert parameters for a sensor, according to embodiments discussed herein. This configuration may be accomplished through the functionalities of a configuration engine as described herein.

In the example of FIG. 8, a lower threshold 802 and an upper threshold 804 of a safe temperature range may be specified by the user.

Further, an estimate product temperature 806 may be specified by the user. This estimate product temperature 806 may be a parameterization of a parameter or variable to be used in the formulae discussed above (e.g., it may be a parameterization of a value for k in the formula for Newton's law of cooling discussed above). In alternative embodiments, this field may be used to enter the actual value for the parameter or variable). This value may correspond to the heat transfer characteristics of the good being monitored corresponding to the sensor. Values for this field may be provided by a vendor of the system and/or be set based on prior experience with and/or knowledge of the particular good being monitored.

The display 800 may also allow for the configuration of one or more alert triggers. Preliminarily, an alert trigger type 808 may be set. This alert trigger type 808 may be, for example, a trigger type that alerts a user based on an amount of time that a sensed characteristic (e.g., an average air temperature and/or an average estimated product temperature) has been outside the range between the lower threshold 802 and the upper threshold 804 (the "alert condition"). As shown, a plurality of alert trigger behaviors 810-814 may be specified relative to this configuration. For example, the first alert trigger behavior 810 has been turned on and is set to send an email after the alert condition has been met for 30 minutes. The second alert trigger behavior 812 has been turned on and is set to make a phone call after the alert condition has been met for 60 minutes. The third alert trigger behavior 814 has been turned on and is set to make a phone call after the alert condition has been met for 90 minutes.

The display 800 may also include other notification options. For example, an updates while active 816 behavior may be set to continue sending recurring alerts every given time period specified by the user while an alert condition is active. A notify when alert conditions end 818 behavior may be set to send an alert when the alert condition ends. A notify when alert resolved 820 behavior may be set to send an alert when a user of the system indicates to the system that the alert has been resolved (discussed below). The display 800 may also include other options, such as an alert pause schedule 822, which may be useful to pause the alert as configured during pre-determined times (to avoid sending alarms during these times)

Figure 9:
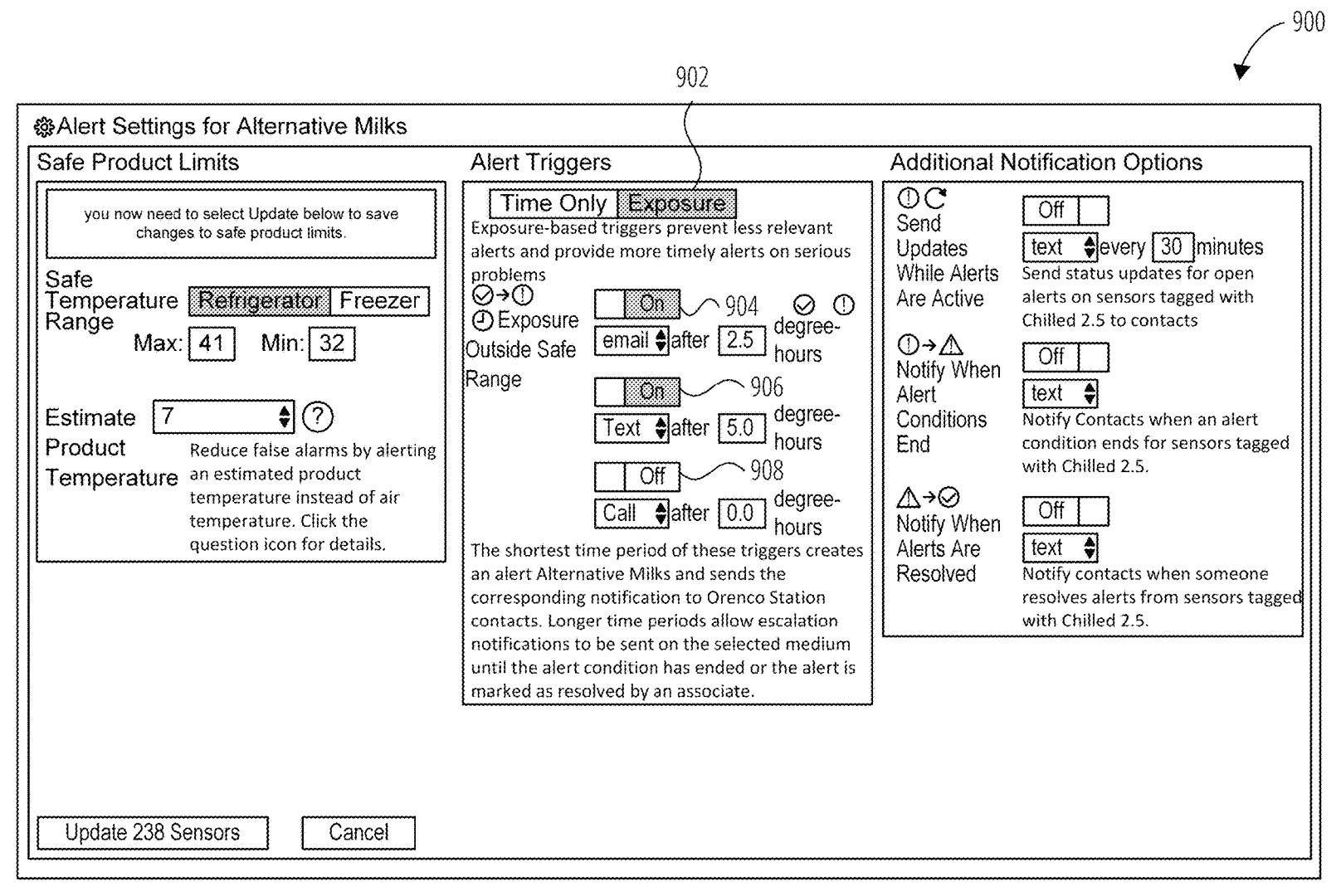

FIG. 9 illustrates a display 900 for configuring alert parameters for a sensor, according to embodiments discussed herein.

The display 900 may be similar to the display 800 of FIG. 8. However, the display 900 may instead have an alert trigger type 902 that is based on exposure (rather than based on time, as in the alert trigger type 808 of FIG. 8). The alert trigger type 902 may send an alert based on one or more alert trigger behaviors 904-908 that trigger based on an exposure calculation. For example, the first alert trigger behavior 904 has been turned on and is set to send an email after 2.5 degree-hours of exposure have been calculated. The second alert trigger behavior 906 has been turned on and is set to send a text message after 5.0 degree-hours have been calculated. The third alert trigger behavior 908 is turned off, and therefore will not send an alert.

A system according to embodiments herein may be further configured to collect audit data relevant for auditing purposes. This audit data may be included in, for example, audit data of a controller platform as described herein. The audit data collection and response features described herein may be performed by, for example, an audit engine of the system.

FIG. 10 illustrates a display 1000 for providing audit data in the form of alert resolutions, according to an embodiment. The display 1000 may include an issue summary 1002 that includes a current status 1004, an issue cause 1006, an alerts record 1008, a graph display link 1010, and a resolution button 1012. The issue summary 1002 may correspond to an ongoing issue that has been determined to be a problem and/or that is generating one or more alerts based on sensor readings of a sensor.

The current status 1004 may disclose the current status of an issue (e.g., ongoing, unresolved, or resolved). The issue cause 1006 may describe the details of the alert condition(s) corresponding to the issue. The alerts record 1008 may show the alerts that were made relative to the issue (e.g., via an alerts engine, as discussed above). The graph display link 1010 may link a user of the system to a graph with a data region showing the data points collected and/or calculated over the period of time corresponding to the alert(s) (as previously discussed).

The resolution button 1012 may allow the user to enter a resolution for the one or more alerts of the issue. This resolution may include a text description. The text description may be a pre-arranged text description that is provided as an option to the user by the system (e.g., as set an administrator of the system). For example, in the refrigeration context, such text may include "refrigeration equipment failure," "door left open," "case cleaning," or "long defrost cycle." It is contemplated that any other pre-set text descriptions (e.g., related to humidity sensors, related to non-refrigeration contexts, etc.) could be set by, e.g., the administrator of the system. Alternatively, this text description may be entered free-form by the user. In some embodiments, the resolution for the alert may alternatively be sent to the system via voice, text, email, or other outside software (e.g., via an API). It is contemplated that the resolution entered by the user may correspond to multiple alerts. For example, when a resolution is entered using the resolution button 1014, that resolution may apply to each of the first alert 1016 and the second alert 1018.

An audit engine may also collect data such as the identity of the user who is providing the resolution, and the time of day that the resolution is being provided. This information may also be stored in the user audit data of the system.

Once a resolution is provided to the audit engine of the system (either via the resolution button 1012 or another described method), the issue may be changed to a "resolved" status and/or the messaging related to the alert(s) (calls, texts, emails, etc., as described above) corresponding to the issue may cease.

It is further contemplated that audit data may further include, for example, pictures taken by the system of the equipment, classification information of equipment, data regarding local weather (as sourced from, e.g., the user and/or a network on which the system communicates, such as the network 158 of FIG. 1), the time at which the resolution began and/or ended, the duration of an alert and/or issue, or other context data relevant to the monitoring of an environmentally controlled area. In some embodiments, some audit data may also be included in one or more alerts sent out by the system (where such audit data is available at the time of the alert).

A system may also use a recognition engine, as described above. The recognition engine may be a recognition engine of a controller platform of the system. The recognition engine may be able to recognize (e.g., make a prediction) about an alert condition that may potentially be reached prior to the alert condition being reached in reality (e.g., of a "potential alert").

The recognition engine may use past data and current trends in the data to perform these functions. For example, a recognition engine may be able to predict, based on past and current data, a potential alert related to, for example, one or more predicted sensor humidity readings, one or more predicted sensor temperature readings, and/or one or more predicted estimated product temperature data points. This may allow the recognition engine to send an alert prior to the time at which an alert may be sent using embodiments previously described above. The recognition engine may work through, for example, one or more functionalities of an alerts engine to have these alerts sent.

In order to perform these recognitions, a recognition engine of the system may take as input, for example, the temperature data over time for a sensor, the humidity data over time for a sensor, an estimated product temperature of a product over time for a product associated with the sensor, degree-hours exposure calculations over time, and/or estimated bacterial growth exposure calculations over time as stored in, for example, a data store of the system as collected sensor data (as described above). This recognition engine may also take in one or more Nth order derivatives of this data over time (as these derived data sets are described above).

A recognition engine of the system may also take as an input time of day data. This time of day data may be provided by a clock of the system (e.g., the clock 108 of FIG. 1). It may also be provided to the recognition engine over a network (e.g., the network 158 of FIG. 1).

A recognition engine of the system may also take as input any user audit data of the system (as that data is described above).

A recognition engine of the system may also take as input any training data (e.g., the training data 122 of FIG. 1). This training data may include, for example, collected temperature over time, estimated product temperature over time, and/or exposure data over time (an derivatives from each of these) that represents situations for which the recognition engine should account. This training data may have been manually collected by a user of the system and/or collected by the activities of the recognition engine and/or the data collection engine.

The recognition engine may use one or more neural networks (NN) to analyze these inputs to determine one or more predicted data points that is expected in the future based on past data and/or current trends in the data. A NN may include a model of one or more nodes which intercommunicate and which each respond to data sent to them according to one or more weights. Nodes of the NN may be input nodes (to accept input), intermediate nodes, and/or output nodes. Incoming data (e.g., a data set over time) to the NN may traverse through and be affected by such nodes according to the weights used by the nodes, such that a corresponding predictive set of data points is generated by the NN. By way of example, it may be that a recurrent neural network (RNN) is selected for this for use with systems described herein, because a RNN may be well suited to determining the one or more predicted data points over time based on an incoming set of data over time.

Such predicted data sets may include predicted data points for future temperature readings over time, each corresponding to a future timestamp (a timestamp for a time that has not yet occurred). It is further contemplated that in some embodiments, future humidity readings over time, future good temperature over time, and/or future good exposure over time (each with corresponding future timestamps) may be predicted in a similar fashion.

A NN of the recognition engine may need to be trained in order to make it suitable for predicting future data points. Training may involve creating nodes, creating weights used by nodes, and/or modifying weights used by nodes of the NN, such that the NN develops a network of nodes that communicate between each other based on a weight between two such nodes. Training may further involve modifying the weight(s) used at one or more individual nodes of the NN in light of an analysis of given data. This training process may be an automatic method that iterates over multiple sets of data in order to create nodes for the NN and/or set the corresponding weight(s) used by those nodes. The training may occur by using information from one or more pieces of training data regarding various parameters of interest (e.g., sensed temperature over time) as covariants during the training process.

In a NN, one or more nodes may be connected in a long chain of cells that allow the time-series data points to flow through the chain. The nodes may contain memory that can influence the outputs of the cell. Each node may merge the values from the previous nodes on potentially several outputs to the inputs of the next node(s) in the chain. The learned weights are used to control various 'gates' in each node in the chain and dictate how much of the inputs from the previous nodes, as well as the stored values in the nodes, should be present on the output(s).

The weights may be arrived at by running a large number of historical data over time values through the NN and attempting to get the NN to yield a set of future time series that match known "future" results. For example, if a 300 point sample from actual data over time is used, 250 points might be used to act as "observed" data, with 50 points used as the "future" data to predict. A training algorithm, for example, backpropagation, may run a training sample through the NN multiple times, or "epochs", and measure the output of the NN against the target set to determine how well can it predict the (known) "future" time series from the target data. Any reported differences may then be used by the algorithm to adjust the weights of one or more nodes for the next run. This process can be run over any number of sets of training data (including a very large number of sets). The training of the algorithms may take a long time and may be re-run whenever the system discovers significantly divergent data when comparing real outcomes vs. the predicted outcomes.

The NN may be trained with data sampled from the training data of the system. The training data may include training data manually collected by the user. The training may also include a selection of data from the sensor data of the system (perhaps as influenced by the user audit data of the system). This includes sensor data over time that corresponds to or is calculated from to the actual sensed values. For example, a set of data over time corresponding to estimated product temperature, derivatives of actually sensed temperature over time, derivatives of product temperature over time, and/or derivatives of product exposure with respect time (as previously discussed) may be used to train a NN.

This training data may have long lookback windows, as temperature data may have long "deserts" in-between dynamic events. This training may take into account a weighting of each data set of the training data, which may have been set by the user or generated automatically by the recognition engine, and may provide such weighting to the NN for use when training.

The selections of sensor data used in the training data may have been copied to the training data manually by a user, and/or copied to the training data by an automated process of the recognition engine. For example, such a process may be programmed to look for abnormal fluctuations and/or patterns in the sensor data and copy such portions of the data to the training data.

As another source of training data, a process of the recognition engine may be programmed to look for context data corresponding to certain user audit data and copy the sensor data corresponding to such user audit data to the training data. For example, the textual narrative associated with a resolution provided by a user in the audit data may indicate that the sensor data collected relative to an alert was not reflective of a situation that caused a real-world issue for the monitored product. In these cases, the recognition engine may be able to add this data to the training data such that future uses of the training data by the NN take this data set into account (at least relative to that product). This data may be weighted based on the user who provided the resolution (e.g., the system may weight data corresponding to a resolution by a recognized "expert" about good quality above the data corresponding to a resolution provided by a person who is not so recognized) with the effect that the NN gives such weighted data a corresponding greater or lesser weight when using it to train and/or make predictions.

The training may also (or additionally) occur by the recognizing and storing patterns discovered in the training data during the training process. For example, when an overall pattern is discovered in the training data, weights of one or more of the nodes of the NN may be changed to de-emphasize (or alternatively to further emphasize) the effect of similar patterns on the output of the NN.

This training may generate one or more models comprising nodes for the NN to use. Once the NN models are trained, one or more predicted data points is computed based on the one or more of the models. The model used to make the prediction may be one or more of the models (including its associated weighting) that were developed according to the training process described above. The model may be provided a set of data over time and asked to use it to predict a future set of data over time. For example, the model may be provided a set of temperature or humidity data over time and make a prediction for a set of values over time for these data types. Other derived data set types used to train the model (for example, product temperature over time, exposure over time, and/or derivatives of these data sets with respect to time) may also be fed to the model, which may yield the prediction of that type as a series of data points corresponding to times in the future. Alternatively, a prediction for these derived data set types may be made based on an analysis of, for example, the predicted temperature data, using methods described above.

Given the possibility of a significant computation time that may be needed in some cases to predict a future set of data over time, running such a prediction on every set of data may not be desirable. It may be that, prior to invoking the prediction process described above, a more simple set of rules may be used to "pre-filter" a set of data to prevent invoking the NN prediction methods in cases where it may not be worth the computation time and expense. For example, NN prediction methods may not be invoked on a set of data over time if, e.g., the previous n time series values are between the thresholds set, and/or computing a rolling mean, median, and max deviations or the previous m set of points are within a set of known values that have statistically resulted in an incorrect or otherwise negative prediction when tested with a NN model.

In some cases, a subset of the most recently gathered data over time (for example, 50 to 80 of the most recently gathered data points) may be used by the NN to generate the one or more predicted data points in this manner. In some embodiments, 20 to 30 data points may be predicted.

Because this process may be computationally expensive, a recognition engine may not predict data points when current data points are well within threshold tolerances (as described above) and/or there is not currently an ongoing issue and/or a recent alert.

The recognition engine may communicate its predicted results with a data collection engine of the system. The data collection engine may then perform calculations on this predictive data similarly as it would on any other data as described above by appending the predictive data immediately forward to its analogous, non-predictive data (e.g., data that has actually gathered by a data collection engine of the system). Accordingly, the analysis methods using a data set over time as described above may be used with predictive data and/or a combination of non-predictive and predictive data.

For example, if the recognition engine provides the data collection engine with a prediction of future temperature readings (and their associated future timestamps), the data collection engine may calculate a predicted temperature of the good over time (along with associated timestamps) corresponding to these predicted temperature readings (by treating data all associated with future timestamps as merely a continuation of the data set and performing the actions describe above). One example of this similar treatment may be, for example, the case where a predicted product temperature at a given timestamp late in the predictive set may be affected by a calculated (current) estimated product temperature and a predictive product temperature earlier in the predictive set—in this case both values may be used normally without materially distinguishing between the non-predictive/predictive nature of the data points.

Further, this predicted temperature of the good over time data could be used by the data collection engine to calculate a predicted exposure of the good over time data that extends into the future (by treating the predicted temperature of the good over time data as a continuation of the non-predictive estimated temperature of the good over time data). For example, the data collection engine may identify one or more future timestamps for which the predicted future temperature of the good is outside the threshold, sum, across these one or more future timestamps, the product of a difference between one of the future timestamps and a previous timestamp (regardless of whether the previous timestamp has passed or is in the future) and a difference between the predicted future temperature of the good at the future timestamp of the one or more future timestamps and the threshold, and adding the result of the summing to a current exposure of the good that has already been calculated.

Figure 11:
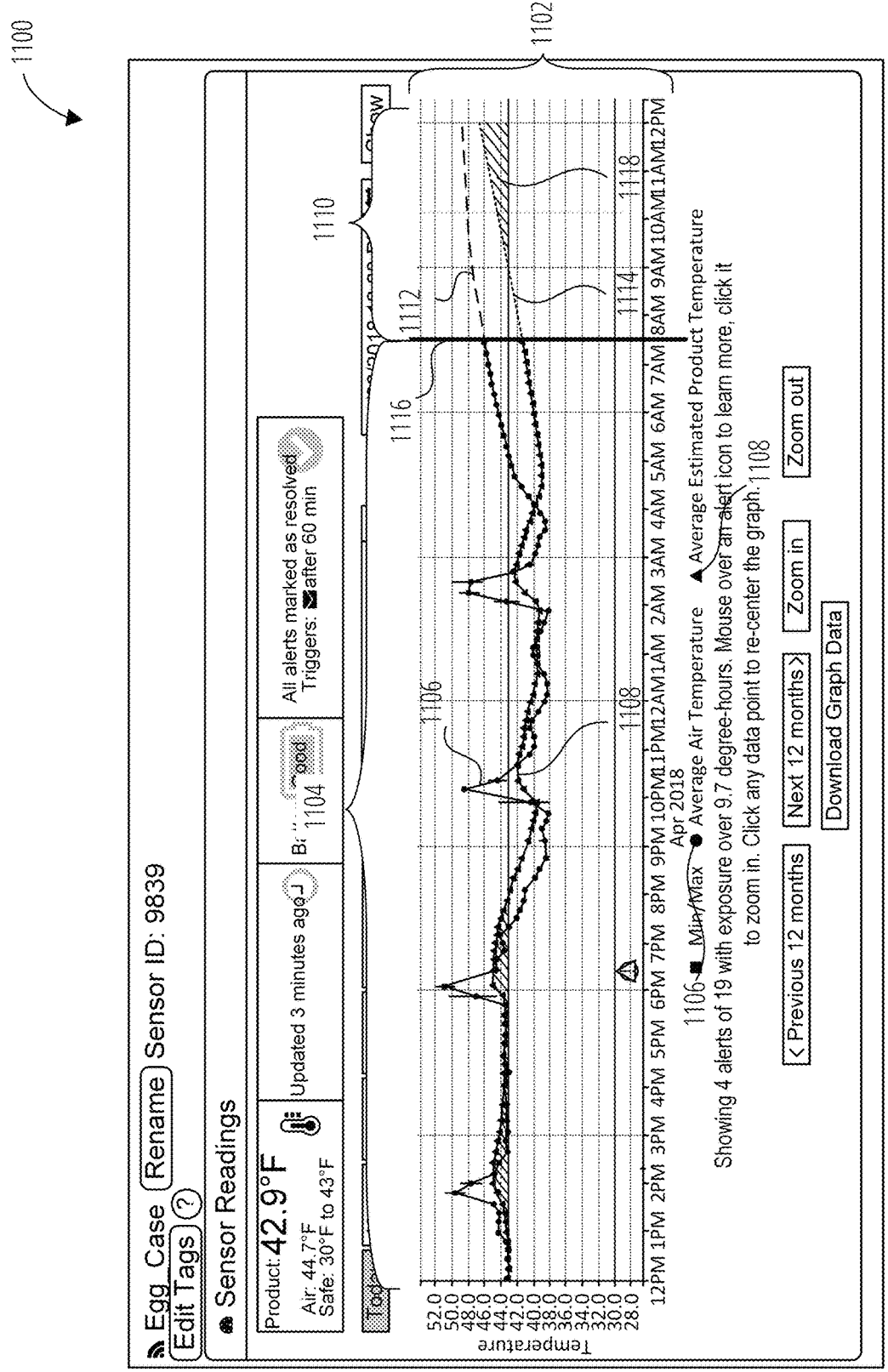
FIG. 11 illustrates a display corresponding to a prediction of future data points according to one embodiment.

This analytical concatenation of current and predictive data may also facilitate the display and use of the predictive data in a useful manner. FIG. 11 illustrates a display 1100 corresponding to a prediction of future data points according to one embodiment. A data region 1102 of the display 1100 may include a first portion 1104 corresponding to a display of actual data measurements of a sensor (e.g., average air temperature over time 1106 as measured by the sensor) and any attendant data therefrom calculated (e.g., the estimated product temperature over time 1108 calculated using the average air temperature over time 1106). A second portion 1110 of the display 1100 may correspond to a display of predictive data measurements (e.g., the predicted average air temperature over time 1112 for the future) and any attendant data therefrom calculated (e.g., the predicted product temperature over time 1114 calculated from the predicted average air temperature over time 1112). The first portion 1104 and the second portion 1110 may be separated by a visual indicator 1116. The recognition engine may provide data to a display engine of the system so that the display engine may generate the display 1100.

This predictive data may be shared by the system with an alerts engine. The alerts engine may use one or more of the predicted data points as compared to pre-established thresholds in order to generate one or more alerts to one or more users over time, similar to the uses of, e.g., the actual average air temperature, the average estimated product temperature, and/or the calculated exposure levels to do so (as described above). For example, the alerts engine may trigger an alert once one or more of the predicted average air temperature over time 1112, the predicted product temperature over time 1114, and/or a predicted exposure of the good (e.g., as calculated corresponding to all or part of the area 1118) exceed given thresholds.

The use of these types of predictive alerts may extend the time for one or more users to react to the predicted alert condition (as compared to the case where the alert conditions described above may be actually reached, as described above). For example, it is contemplated that these predictive alerts may allow for a response to an alert from 1.5 to 2.5 hours sooner than otherwise would be possible. Further, the ability to predict in this fashion may make a user more comfortable with the use of looser alert conditions (by negating any reason to hold alert conditions artificially tight in a case where these predictive alerts were not available in order to get an earlier alert). For example, if the prediction engine using the methods described above forecasts exposure with relatively high accuracy based on past events, then lower exposure events (which in themselves do not rise to the level of an alert condition) need not to be used to create an alert with the desired timing. This may ameliorate the side effect of "false alarm" alerts from the system when the system is used with artificially tight alert conditions.

A recognition engine of a system according to embodiments herein may also be programmable in order to recognize an issue that goes beyond the sensor readings/calculations cases discussed above and react accordingly (change a display on a display device of the system, send an alert to a user of the system, etc.). Information that goes beyond the sensor readings/calculations of the data collection engine may be considered "context" data. This recognition engine may work through elements of an alerts engine as described in order for the system to provide alerts based on these outside "contexts." Alternatively or additionally, the recognition engine may log this data for review by a user at a later time.

The recognition engine may further use one or more NNs to "learn" to alert based on a recognition of a situation involving an outside context. The NN so used may "train" on "normal" data from the training data of the system and then work through the alerts engine of the system to send an alert when an abnormal reading involving an outside context occurs. For example, the system may learn to recognize, for example, the system failure events described herein by training on data about "normal" operation gathered over time to the temperature readings and/or calculated temperatures of a good and recognizing that current characteristics are outside a certain number of standard deviations away from the "normal" operation condition. In other cases, the outside context for which the recognition engine should check may be provided to the system via a parameter and/or programming.

In one example of alerting based at least in part on an outside context, a recognition engine of a system according to embodiments herein may infer information about one or more refrigeration compressors using temperature data. The system may be configured to track rates of change of temperature at a given temperature sensor or sensors over a long period of time, in the manner described above. Comparing as between individual portions of this long-term data, a recognition engine of the system may be capable of recognizing, for example, that a temperature reading at a certain sensor or sensors does not drop as quickly has it has in the past under similar circumstances. The system may then use this information to infer, e.g., that a compressor associated with the temperature sensor or sensors is not running in optimal condition and send a corresponding alert to a user.

The recognition engine of the system may further go on to estimate information about the compressor. For example, the system may be able to use temperature rate of change data (as calculated by the data collection engine) to estimate the power draw of the compressor. Power levels for multiple compressors associated with the temperature sensors of the system may each be calculated in this way and provided to the user either separately or in aggregate via an alert when an anomaly occurs. The recognition engine of the system may further use the temperature rate of change data to calculate a confidence level/expected time of failure for the compressor. These calculations may be further informed in part based on data gathered over time about the compressors either by the system or by the user (and subsequently provided to the system).

Another example of alerting based at least in part on an outside context may involve, for example, a refrigerator in a grocery store or restaurant. It might be expected that a temperature and/or humidity inside the refrigerator might fluctuate during business hours as customers and/or employees open the refrigerator in order to retrieve goods. The system may therefore be configured not to alert based on a measured temperature and/or humidity directly (which may lead to constant alerting when the refrigerator is in heavy use), but rather to alert based on, for example, a calculated exposure level of the goods in the refrigerator. However, it may be that a recognition engine of the system is programmed to monitor the time of day. It may further be programmed to cause the alerts engine to alert immediately upon crossing a sensor threshold when the threshold is crossed outside of business hours (when there is no reason the sensor reading should be outside the threshold). It is further contemplated that a NN of the recognition engine may have learned the behavior automatically over time after recognizing the pattern that the user ignores direct temperature and/or humidity alerts during business hours but is immediately responsive to such alerts after business hours. The NN may have arrived at this conclusion via mere pattern recognition, or alternatively may have been helped to learn this due to resolutions reflected in audit data of the system.

A system according to embodiments herein may monitor patterns across multiple sensors and alert based on these overall patterns (e.g., using a recognition engine). This may allow the system to respond to acute, wide-ranging issues faster than would be possible when monitoring individual sensors. For example, a system monitoring patterns across multiple temperature and/or humidity sensors may notice that a temperature rise (or fall) and/or humidity rise (or fall) has begun to occur at the same time across multiple sensors. As another example, a system monitoring patterns across multiple temperature sensors may notice that an exposure rise has begun to occur at the same time across multiple sensors. As yet another example, a system monitoring patterns across multiple temperature sensors may notice that a predicted temperature rise or a predicted exposure rise is predicted to begin to occur at the same time across multiple sensors.

Any of these changes, taken individually, may not (or at least, not yet) appear as an alertable issue (e.g., they may individually appear similar to an expected defrost cycle). However, monitoring for patterns across multiple sensors allows a system in this situation to infer, due to the simultaneous nature of the changes, that a larger system problem (e.g., a compressor has gone out, a power outage, or controller failure) has occurred. The system may then immediately respond using the alerting methods (e.g., using an alerts engine) disclosed herein without waiting for any individual sensor (or a calculation based on that sensor's readings, such as an exposure level of a good associated with one temperature sensor) to reach its individual alert condition.

It may be that, e.g., a NN of the recognition engine may have learned, based on the training data, that this type of simultaneous temperature rise (or fall) does not happen under normal conditions, and accordingly may immediately alert the user based on this new, anomalous behavior detected across multiple sensors without waiting for set thresholds to be passed. The NN may assign a probability that there is an issue based on its learning, and may trigger such alerts when the assigned probability meets or surpasses a certain threshold.

The alerts engine may then send alerts related to conditions across multiple sensors to one or more users according to a priority, analogously as discussed above. In other words, the alerts engine may send first alerts of this type (with a lower priority) to one or more users, and may subsequently send additional alerts of this type (with a higher priority) to one or more users as conditions stray further from the "normal" condition (e.g., as determined by a NN, as described above).

In some cases where the recognition engine is monitoring for patterns across more than one sensor, it may be desirable to monitor and trigger based on the readings directly reported by the sensors rather than, e.g., the estimated temperature of a good and/or exposure level of the good that is being calculated by the system. This is because there may be a lag in the calculation of the temperature and/or exposure of the good vs. the environmental state, and an acute event that merits an alert may be capable of being inferred from a comparison of the immediate sensor data (which arrives in practically real time) rather than the calculations derived from that sensor data (which may be subject to data "smoothing" and thus not immediately reflect the extent of real-time environmental change).

The automation of the collection and storage of environmental readings along with these (and other) pieces of data may permit the accumulation of large data sets. Different algorithms applied to these data sets may reveal patterns and correlations that in turn may lead to actions suggested by the system to the user (perhaps in the form of an alert as discussed above) to ameliorate any observed problems. Possible uses for this data include energy management, gaining further insight (beyond direct environmental considerations) into equipment operation (as in the contextual decisions enabled above), problems with operating procedures relating to the monitored device, integration of the data with repair workflows, etc. This data may be generated through analysis by a NN of a recognition engine (or other element of the system), as described above. This data may be stored as training data of a controller platform of the system.

Figure 12:
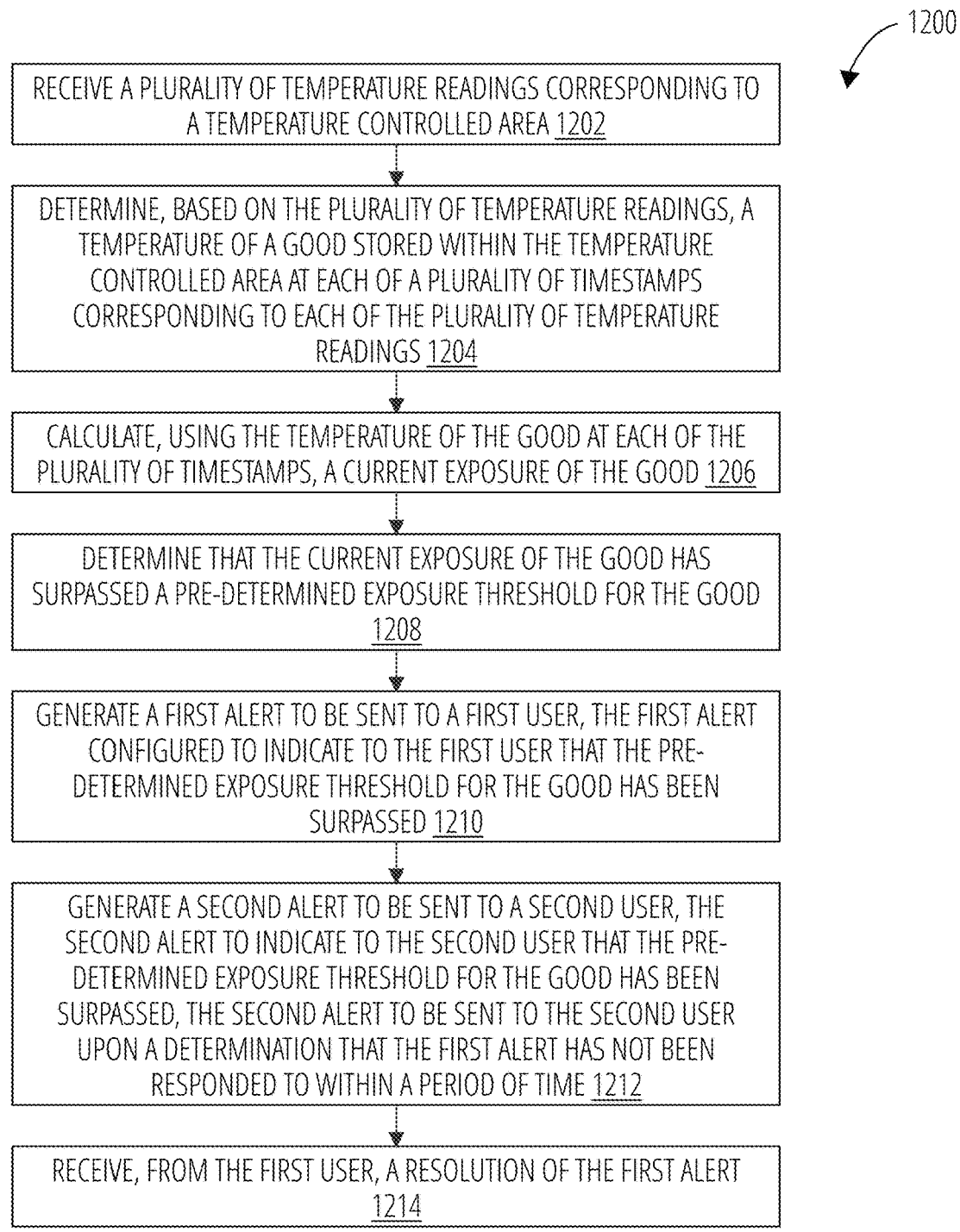
FIG. 12 illustrates a method of a system according to some embodiments herein.

FIG. 12 illustrates a method 1200 of a system according to some embodiments herein. The method 1200 includes receiving 1202 a plurality of temperature readings corresponding to a temperature controlled area.

The method 1200 includes determining 1204, based on the plurality of temperature readings, a temperature of a good stored within the temperature controlled area at each of a plurality of timestamps corresponding to each of the plurality of temperature readings.

The method 1200 includes calculating 1206, using the temperature of the good at each of the plurality of timestamps, a current exposure of the good.

The method 1200 includes determining 1208 that the current exposure of the good has met a pre-determined exposure threshold for the good.

The method 1200 includes generating 1210 a first alert to be sent to a first user, the first alert configured to indicate to the first user that the pre-determined exposure threshold for the good has been met.

The method 1200 includes generating 1212 a second alert to be sent to a second user, the second alert to indicate to the second user that the pre-determined exposure threshold for the good has been surpassed, the second alert to be sent to the second user upon a determination that the first alert has not been responded to within a period of time.

The method 1200 includes receiving 1214, from the first user, a resolution of the first alert.

Figure 13:
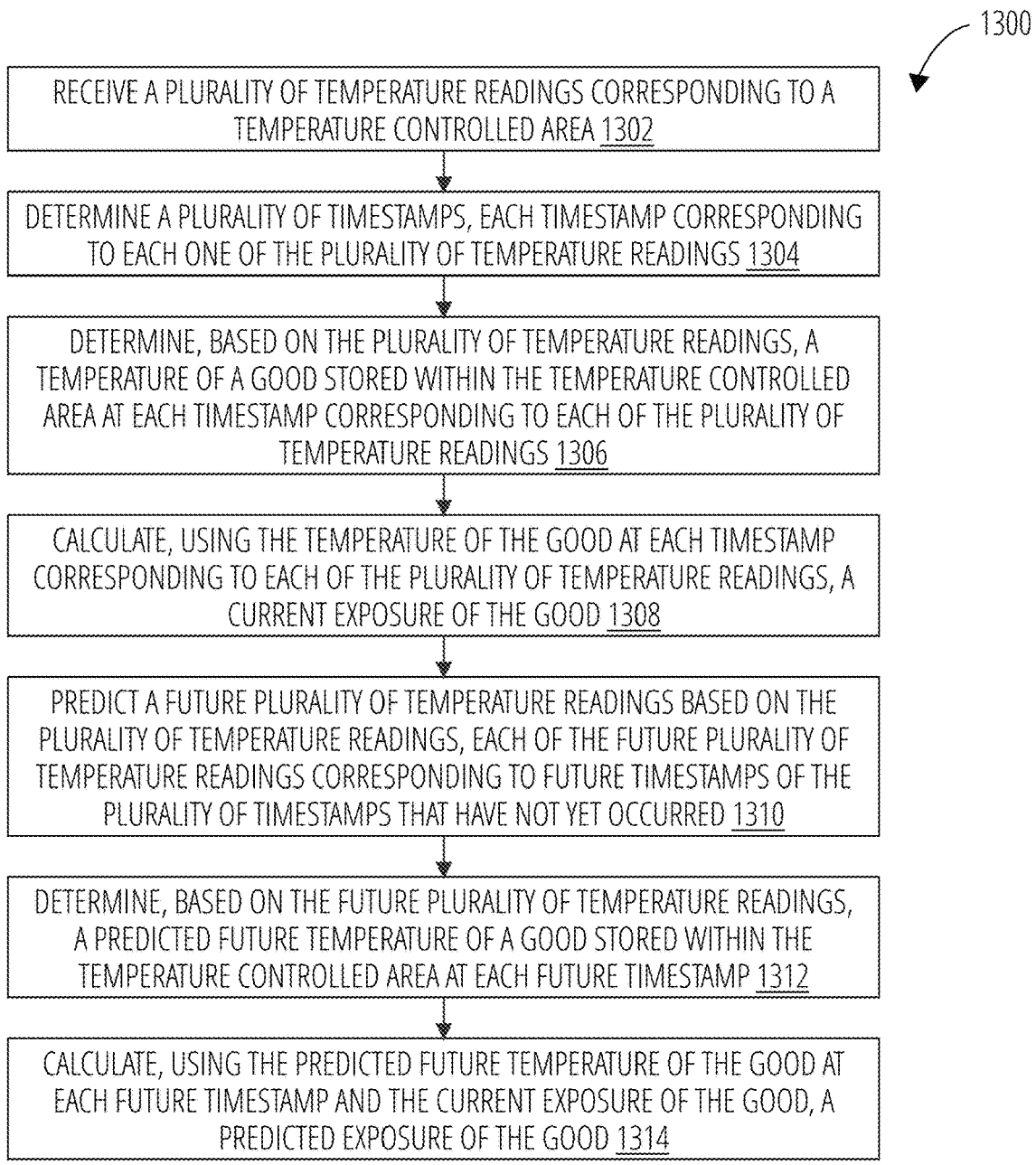
FIG. 13 illustrates a method of a system according to some embodiments herein.

FIG. 13 illustrates a method 1300 of a system according to some embodiments herein.

The method 1300 includes receiving 1302 a plurality of temperature readings corresponding to a temperature controlled area.

The method 1300 includes determining 1304 a plurality of timestamps, each timestamp corresponding to each one of the plurality of temperature readings.

The method 1300 includes determining 1306, based on the plurality of temperature readings, a temperature of a good stored within the temperature controlled area at each timestamp corresponding to each of the plurality of temperature readings.

The method 1300 includes calculating 1308, using the temperature of the good at each timestamp corresponding to each of the plurality of temperature readings, a current exposure of the good.

The method 1300 includes predicting 1310 a future plurality of temperature readings based on the plurality of temperature readings, each of the future plurality of temperature readings corresponding to future timestamps of the plurality of timestamps that have not yet occurred.

The method 1300 includes determining 1312, based on the future plurality of temperature readings, a predicted future temperature of a good stored within the temperature controlled area at each future timestamp.

The method 1300 includes calculating 1314, using the predicted future temperature of the good at each future timestamp and the current exposure of the good, a predicted exposure of the good.

Figure 14:
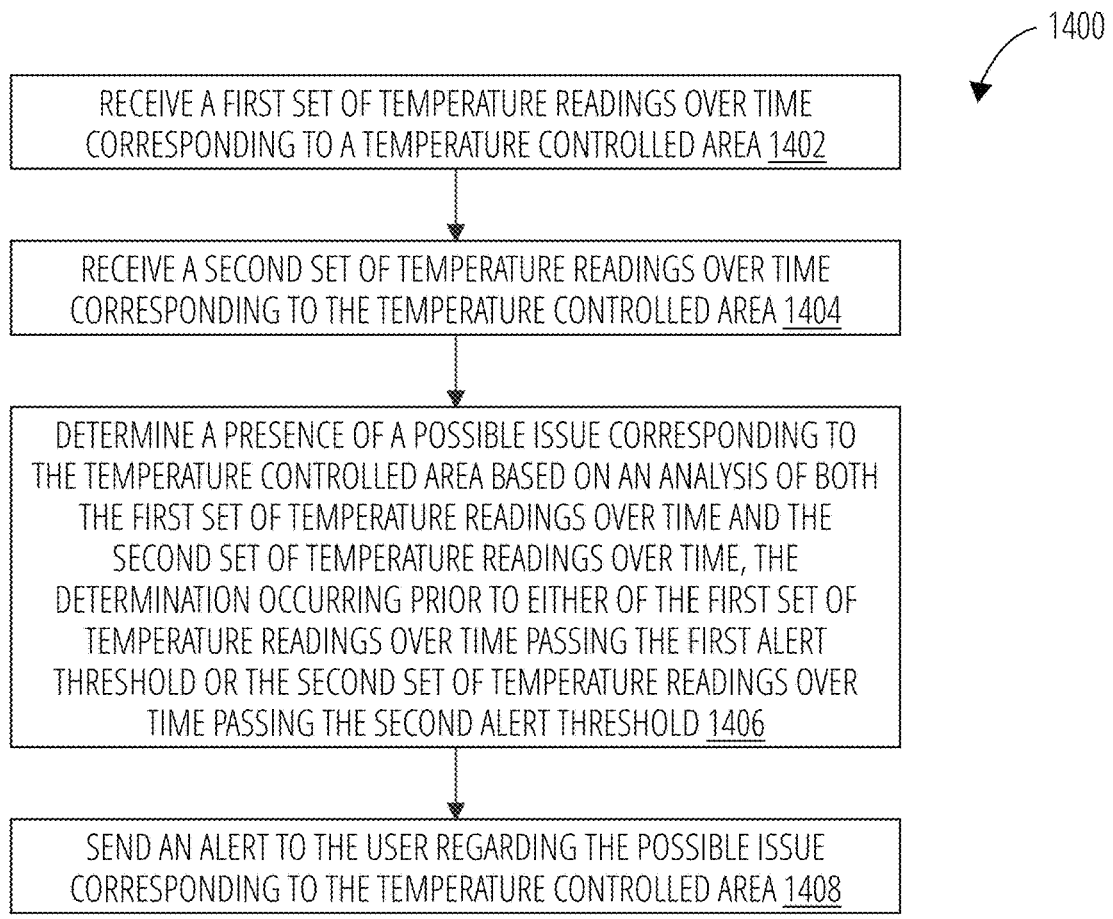
FIG. 14 illustrates a method of a system according to some embodiments herein.

FIG. 14 illustrates a method 1400 of a system according to some embodiments herein.

The method 1400 includes receiving 1402, a first set of temperature readings over time corresponding to a temperature controlled area.

The method 1400 includes receiving 1404, a second set of temperature readings over time corresponding to the temperature controlled area.

The method 1400 includes determining 1406 a presence of a possible issue corresponding to the temperature controlled area based on an analysis of both the first set of temperature readings over time and the second set of temperature readings over time, the determination occurring prior to either of the first set of temperature readings over time passing the first alert threshold or the second set of temperature readings over time passing the second alert threshold.

The method 1400 includes sending 1408 an alert to the user regarding the possible issue corresponding to the temperature controlled area.

The foregoing specification has been described with reference to various embodiments, including the best mode. However, those skilled in the art appreciate that various modifications and changes can be made without departing from the scope of the present disclosure and the underlying principles of the embodiments disclosed herein. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

In some embodiments, a system includes a computing device configured to execute a software program configured to instruct the computing device to implement embodiments of the disclosure. For example, the computing device may include at least one processor and at least one data storage device having computer-readable instructions stored thereon. The computer-readable instructions may be configured to instruct the at least one processor to perform operations and functions discussed herein. By way of non-limiting example, the computer-readable instructions may be configured to instruct the at least one processor to display, on a screen of a display device, a GUI as illustrated in FIG. 5 through FIG. 10.

As used herein, the terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus.

Embodiments herein may include various engines, which may be embodied in machine-executable instructions to be executed by a general-purpose or special-purpose computer (or other electronic device). Alternatively, the engine functionality may be performed by hardware components that include specific logic for performing the function(s) of the engines, or by a combination of hardware, software, and/or firmware.

Principles of the present disclosure may be reflected in a computer program product on a tangible computer-readable storage medium having stored instructions thereon that may be used to program a computer (or other electronic device) to perform processes described herein. Any suitable computer-readable storage medium may be utilized, including magnetic storage devices (hard disks, floppy disks, and the like), optical storage devices (CD-ROMs, DVDs, Bluray discs, and the like), flash memory, and/or other types of medium/machine readable medium suitable for storing electronic instructions. These instructions may be loaded onto a general-purpose computer, special-purpose computer, or other programmable data processing apparatus to produce a machine, such that the instructions that execute on the computer or other programmable data processing apparatus create means for implementing the functions specified. These instructions may also be stored in a computer-readable memory that can direct a computer or other programmable data processing apparatus to function in a particular manner, such that the instructions stored in the computer-readable memory produce an article of manufacture including instruction means that implement the function specified. The instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified.

Principles of the present disclosure may be reflected in a computer program implemented as one or more software modules or components. As used herein, a software module or component may include any type of computer instruction or computer-executable code located within a memory device and/or computer-readable storage medium. A software module may, for instance, comprise one or more physical or logical blocks of computer instructions, which may be organized as a routine, a program, an object, a component, a data structure, etc., that perform one or more tasks or implement particular data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the embodiments disclosed herein may be provided by those of skill in the pertinent art(s) using the teachings presented here and programming languages and tools, such as Java, JavaScript, Pascal, C++, C, database languages, APIs, SDKs, assembly, firmware, microcode, and/or other languages and tools.

Embodiments as disclosed herein may be computer-implemented in whole or in part on a digital computer. The digital computer includes a processor performing the required computations. The computer further includes a memory in electronic communication with the processor to store a computer operating system. The computer operating systems may include, but are not limited to, MS-DOS, Windows, Linux, Unix, AIX, CLIX, QNX, OS/2, and MacOS. Alternatively, it is expected that future embodiments will be adapted to execute on other future operating systems.

It will be apparent to those having skill in the art that many changes may be made to the details of the above-described embodiments without departing from the underlying principles of the embodiments disclosed herein.

What is claimed is:

1. A system for environmental monitoring and performing environmental-related calculations, comprising:
   one or more processors;

a network interface;
a memory in electrical communication with the one or more processors, the memory to store an electronic message to be sent to a user;
a data collection engine to:
  receive a plurality of temperature readings taken at a temperature controlled area;
  determine a plurality of timestamps, each timestamp corresponding to each one of the plurality of temperature readings;
  determine, based on the plurality of temperature readings, a temperature of a good stored within the temperature controlled area at each timestamp corresponding to each of the plurality of temperature readings; and
  calculate, using the temperature of the good at each timestamp corresponding to each of the plurality of temperature readings, a current exposure of the good; an alerts engine to:
  determine that the current exposure of the good has surpassed a pre-determined exposure threshold for the good; and
  generate the electronic message to be sent to the user by the network interface in response to determining that the current exposure of the good has surpassed the pre-determined exposure threshold for the good, the electronic message configured to indicate to the user that the pre-determined exposure threshold for the good has been surpassed; and
a recognition engine to:
  predict a future plurality of temperature readings based on the plurality of temperature readings, each of the future plurality of temperature readings corresponding to future timestamps of the plurality of timestamps that have not yet occurred;
wherein the data collection engine is further to:
  determine, based on the future plurality of temperature readings, a predicted future temperature of the good at each future timestamp; and
  calculate, using the predicted future temperature of the good at each future timestamp and the current exposure of the good, a predicted exposure of the good by:
    identifying one or more future timestamps for which the predicted future temperature of the good is outside a temperature threshold;
    summing across the one or more future timestamps a product of a difference between a future timestamp of the one or more future timestamps and a previous timestamp and a difference between the predicted future temperature of the good at the future timestamp of the one or more future timestamps and the threshold; and
    adding a result of the summing to the current exposure of the good.

2. The system of claim 1, wherein the data collection engine calculates the current exposure of the good by using a non-linear formula.

3. The system of claim 1, wherein the data collection engine calculates the current exposure of the good by:
  identifying one or more of the timestamps for which the temperature of the good is outside the temperature threshold; and
  summing across the one or more timestamps a product of a difference between a timestamp of the one or more timestamps and a previous timestamp and a difference between the temperature of the good at the timestamp of the one or more timestamps and the temperature threshold.

4. The system of claim 1, wherein the data collection engine determines the temperature of the good during a timestamp of the plurality of timestamps by using the temperature reading corresponding to the timestamp.

5. The system of claim 1, wherein the data collection engine determines the temperature of the good during a timestamp of the plurality of timestamps based on the temperature of the good at a previous timestamp.

6. The system of claim 1, wherein the recognition engine comprises a recurrent neural network that has been trained on training data of the system, the recurrent neural network to be used by the recognition engine to generate the future plurality of temperature readings.

7. The system of claim 1, the alerts engine further to:
  determine that the predicted exposure of the good has surpassed the pre-determined exposure threshold for the good; and
  generate a second electronic message to be sent to the user by the network interface in response to the determination that the predicted exposure of the good has surpassed the pre- determined exposure threshold for the good, the second electronic message configured to indicate to the user that the pre-determined exposure threshold for the good is predicted to be surpassed.

8. The system of claim 1, wherein:
  a recognition engine is further to monitor patterns across multiple sets of temperature data; and
  the alerts engine is to alert based on data from each of the multiple sets of temperature data.

9. A system for environmental monitoring and performing environmental-related calculations, comprising:
  one or more processors;
  a network interface;
  a memory in electrical communication with the one or more processors, the memory to store a calculated exposure of a good;
  a data collection engine to:
    receive a plurality of temperature readings taken at a temperature controlled area;
    apply a timestamp to each one of the plurality of temperature readings;
    determine, based on the plurality of temperature readings, a temperature of a good stored within the temperature controlled area at each timestamp; and
    calculate, using the temperature of the good at each timestamp, an exposure of the good;
    determine, based on a future plurality of temperature readings, a predicted future temperature of the good stored within the temperature controlled area at each future timestamp; and
    calculate, using the predicted future temperature of the good at each future timestamp and the exposure of the good, a predicted exposure of the good by:
      identifying one or more future timestamps for which the predicted future temperature of the good is outside a temperature threshold;
      summing across the one or more future timestamps a product of a difference between a future timestamp of the one or more future timestamps and a previous timestamp and a difference between the predicted future temperature of the good at the future timestamp of the one or more future timestamps and the temperature threshold; and adding a result of the summing to the current exposure of the good; and a recognition engine to:
predict the future plurality of temperature readings based on the plurality of temperature readings, each of the future plurality of temperature readings corresponding to a future timestamp.

10. The system of claim 9, further comprising:
an alerts engine to:
compare the predicted exposure of the good against a pre-determined exposure threshold; and
generate an alert to be sent to a user by the network interface, the alert configured to indicate to the user that the predicted exposure of the good exceeds the pre-determined exposure threshold.

11. The system of claim 9, further comprising an audit engine to collect alert resolution data from a user of the system.

12. The system of claim 9, the recognition engine further to:
train a neural network of the recognition engine using training data of the system; the training comprising analyzing, at the neural network, patterns found in the training data; said training to be used by the neural network to make the prediction of the future plurality of temperature readings.

13. The system of claim 12, wherein the training data comprises data generated by the neural network.

14. The system of claim 12, wherein the training data comprises data provided to the system by a user of the system.

15. The system of claim 12, the training data comprising one or more of:
temperature data over time previously collected by the system;
estimated good temperature data over time previously calculated by the system; and
exposure data over time previously calculated by the system.

16. A method for environmental monitoring and performing environmental-related calculations, comprising:
receiving a plurality of temperature readings taken at a temperature controlled area;
applying a timestamp to each one of the plurality of temperature readings;
determining, based on the plurality of temperature readings, a temperature of a good stored within the temperature controlled area at each timestamp;
calculating, using the temperature of the good at each timestamp, an exposure of the good;
predicting a future plurality of temperature readings based on the plurality of temperature readings, each of the future plurality of temperature readings corresponding to a future timestamp;
determining, based on the future plurality of temperature readings, a predicted future temperature of the good stored within the temperature controlled area at each future timestamp; and
calculating, using the predicted future temperature of the good at each future timestamp and the exposure of the good, a predicted exposure of the good by:
identifying one or more future timestamps for which the predicted future temperature of the good is outside a temperature threshold;
summing across the one or more future timestamps a product of a difference between a future timestamp of the one or more future timestamps and a previous timestamp and a difference between the predicted future temperature of the good at the future timestamp of the one or more future timestamps and the temperature threshold; and
adding a result of the summing to the current exposure of the good.

17. The method of claim 16, further comprising:
comparing the predicted exposure of the good against a pre-determined exposure threshold; and
generating an alert to be sent to a user, the alert configured to indicate to the user that the predicted exposure of the good exceeds the pre-determined exposure threshold.

18. The method of claim 16, further comprising:
training a neural network using training data; the training comprising analyzing, at the neural network, patterns found in the training data; said training to be used by the neural network to make the prediction of the future plurality of temperature readings.

19. The method of claim 18, wherein the training data comprises one or more of:
previously collected temperature data over time;
previously calculated estimated good temperature data over time; and
previously calculated exposure data over time.

20. The method of claim 16, further comprising collecting alert resolution data from a user.

* * * * *